US010625082B2

(12) United States Patent
Laghi

(10) Patent No.: US 10,625,082 B2
(45) Date of Patent: Apr. 21, 2020

(54) VISUALIZATION OF DEEP BRAIN STIMULATION EFFICACY

(71) Applicant: Boston Scientific Neuromodulation Corporation, Valencia, CA (US)

(72) Inventor: Fabio Laghi, Zürich (CH)

(73) Assignee: BOSTON SCIENTIFIC NEUROMODULATION CORPORATION, Valencia, CA (US)

( * ) Notice: Subject to any disclaimer, the term of this patent is extended or adjusted under 35 U.S.C. 154(b) by 73 days.

(21) Appl. No.: 15/920,153

(22) Filed: Mar. 13, 2018

(65) Prior Publication Data

US 2018/0264278 A1  Sep. 20, 2018

Related U.S. Application Data

(60) Provisional application No. 62/471,540, filed on Mar. 15, 2017.

(51) Int. Cl.
| | | |
|---|---|---|
| A61N 1/372 | (2006.01) | |
| A61N 1/05 | (2006.01) | |
| A61N 1/36 | (2006.01) | |

(52) U.S. Cl.
CPC ........ *A61N 1/37247* (2013.01); *A61N 1/0534* (2013.01); *A61N 1/36067* (2013.01);
(Continued)

(58) Field of Classification Search
CPC ................ A61N 1/372; A61N 1/36185; A61N 1/37247; A61N 1/37252; A61N 1/37241;
(Continued)

(56) References Cited

U.S. PATENT DOCUMENTS

| | | |
|---|---|---|
| 3,999,555 A | 12/1976 | Person |
| 4,144,889 A | 3/1979 | Tyers et al. |

(Continued)

FOREIGN PATENT DOCUMENTS

| | | |
|---|---|---|
| EP | 1048320 | 11/2000 |
| EP | 1166819 | 1/2002 |

(Continued)

OTHER PUBLICATIONS

Nowinski, W. L., et al., "Statistical analysis of 168 bilateral subthalamic nucleus implantations by means of the probabilistic functional atlas.", Neurosurgery 57(4 Suppl) (Oct. 2005),319-30.
(Continued)

*Primary Examiner* — Carl H Layno
*Assistant Examiner* — Jon Eric C Morales
(74) *Attorney, Agent, or Firm* — Lowe Graham Jones PLLC; Bruce E. Black

(57) ABSTRACT

A computing device executes a software program that communicates various deep brain stimulation (DBS) routines to a neurostimulator. The software program generates a graphical user interface (GUI) that receives inputs that are indicative of a patient's response to the various DBS routines. The GUI further includes a representation of each of one or more electrode leads that are connected to the neurostimulator. Based on the patient response inputs, one or more symbols that are indicative of an effectiveness of the stimulation routines are displayed at positions on the lead representations that correspond to parameters of the stimulation routines.

20 Claims, 13 Drawing Sheets

(52) U.S. Cl.
CPC ...... *A61N 1/36132* (2013.01); *A61N 1/36146* (2013.01); *A61N 1/37223* (2013.01)

(58) Field of Classification Search
CPC ............ A61N 1/36003; A61N 1/36014; A61N 1/36071; A61N 1/36082; A61N 1/3688; A61N 1/37264
USPC .......................................................... 607/45
See application file for complete search history.

(56) References Cited

U.S. PATENT DOCUMENTS

| | | | |
|---|---|---|---|
| 4,177,818 A | 12/1979 | De Pedro |
| 4,341,221 A | 7/1982 | Testerman |
| 4,378,797 A | 4/1983 | Osterholm |
| 4,445,500 A | 5/1984 | Osterholm |
| 4,735,208 A | 4/1988 | Wyler et al. |
| 4,765,341 A | 8/1988 | Mower et al. |
| 4,841,973 A | 6/1989 | Stecker |
| 5,067,495 A | 11/1991 | Brehm |
| 5,099,846 A | 3/1992 | Hardy |
| 5,222,494 A | 6/1993 | Baker, Jr. |
| 5,255,693 A | 10/1993 | Dutcher |
| 5,259,387 A | 11/1993 | dePinto |
| 5,304,206 A | 4/1994 | Baker, Jr. et al. |
| 5,344,438 A | 9/1994 | Testerman et al. |
| 5,361,763 A | 11/1994 | Kao et al. |
| 5,452,407 A | 9/1995 | Crook |
| 5,560,360 A | 10/1996 | Filler et al. |
| 5,565,949 A | 10/1996 | Kasha, Jr. |
| 5,593,427 A | 1/1997 | Gliner et al. |
| 5,601,612 A | 3/1997 | Cameron et al. |
| 5,620,470 A | 4/1997 | Gliner et al. |
| 5,651,767 A | 7/1997 | Schulman |
| 5,711,316 A | 1/1998 | Elsberry et al. |
| 5,713,922 A | 2/1998 | King |
| 5,716,377 A | 2/1998 | Rise et al. |
| 5,724,985 A | 3/1998 | Snell et al. |
| 5,749,904 A | 5/1998 | Gliner et al. |
| 5,749,905 A | 5/1998 | Gliner et al. |
| 5,776,170 A | 7/1998 | MacDonald et al. |
| 5,782,762 A | 7/1998 | Vining |
| 5,843,148 A | 12/1998 | Gijsbers et al. |
| 5,859,922 A | 1/1999 | Hoffmann |
| 5,868,740 A | 2/1999 | LeVeen et al. |
| 5,897,583 A | 4/1999 | Meyer et al. |
| 5,910,804 A | 6/1999 | Fortenbery et al. |
| 5,925,070 A | 7/1999 | King et al. |
| 5,938,688 A | 8/1999 | Schiff |
| 5,938,690 A | 8/1999 | Law et al. |
| 5,978,713 A | 11/1999 | Prutchi et al. |
| 6,016,449 A | 1/2000 | Fischell et al. |
| 6,029,090 A | 2/2000 | Herbst |
| 6,029,091 A | 2/2000 | de la Rama et al. |
| 6,050,992 A | 4/2000 | Nichols |
| 6,058,331 A | 5/2000 | King |
| 6,066,163 A | 5/2000 | John |
| 6,083,162 A | 7/2000 | Vining |
| 6,094,598 A | 7/2000 | Elsberry et al. |
| 6,096,756 A | 8/2000 | Crain et al. |
| 6,106,460 A | 8/2000 | Panescu et al. |
| 6,109,269 A | 8/2000 | Rise et al. |
| 6,128,538 A | 10/2000 | Fischell et al. |
| 6,129,685 A | 10/2000 | Howard, III |
| 6,146,390 A | 11/2000 | Heilbrun et al. |
| 6,161,044 A | 12/2000 | Silverstone |
| 6,167,311 A | 12/2000 | Rezai |
| 6,181,969 B1 | 1/2001 | Gord |
| 6,192,266 B1 | 2/2001 | Dupree et al. |
| 6,205,361 B1 | 3/2001 | Kuzma |
| 6,208,881 B1 | 3/2001 | Champeau |
| 6,240,308 B1 | 5/2001 | Hardy et al. |
| 6,246,912 B1 | 6/2001 | Sluijter et al. |
| 6,253,109 B1 | 6/2001 | Gielen |
| 6,289,239 B1 | 9/2001 | Panescu et al. |
| 6,301,492 B1 | 10/2001 | Zonenshayn |
| 6,310,619 B1 | 10/2001 | Rice |
| 6,319,241 B1 | 11/2001 | King |
| 6,336,899 B1 | 1/2002 | Yamazaki |
| 6,343,226 B1 | 1/2002 | Sunde et al. |
| 6,351,675 B1 | 2/2002 | Tholen et al. |
| 6,353,762 B1 | 3/2002 | Baudino et al. |
| 6,366,813 B1 | 4/2002 | DiLorenzo |
| 6,368,331 B1 | 4/2002 | Front et al. |
| 6,389,311 B1 | 5/2002 | Whayne et al. |
| 6,393,325 B1 | 5/2002 | Mann et al. |
| 6,421,566 B1 | 7/2002 | Holsheimer |
| 6,435,878 B1 | 8/2002 | Reynolds et al. |
| 6,442,432 B2 | 8/2002 | Lee |
| 6,463,328 B1 | 10/2002 | John |
| 6,491,699 B1 | 12/2002 | Henderson et al. |
| 6,494,831 B1 | 12/2002 | Koritzinsky |
| 6,507,759 B1 | 1/2003 | Prutchi et al. |
| 6,510,347 B2 | 1/2003 | Borkan |
| 6,516,227 B1 | 2/2003 | Meadows et al. |
| 6,517,480 B1 | 2/2003 | Krass |
| 6,539,263 B1 | 3/2003 | Schiff |
| 6,560,490 B2 | 5/2003 | Grill et al. |
| 6,579,280 B1 | 6/2003 | Kovach et al. |
| 6,600,956 B2 | 7/2003 | Maschino et al. |
| 6,606,523 B1 | 8/2003 | Jenkins |
| 6,609,029 B1 | 8/2003 | Mann et al. |
| 6,609,031 B1 | 8/2003 | Law et al. |
| 6,609,032 B1 | 8/2003 | Woods et al. |
| 6,622,048 B1 | 9/2003 | Mann et al. |
| 6,631,297 B1 | 10/2003 | Mo |
| 6,654,642 B2 | 11/2003 | North et al. |
| 6,662,053 B2 | 12/2003 | Borkan |
| 6,675,046 B2 | 1/2004 | Holsheimer |
| 6,684,106 B2 | 1/2004 | Herbst |
| 6,687,392 B1 | 2/2004 | Touzawa et al. |
| 6,690,972 B2 | 2/2004 | Conley et al. |
| 6,690,974 B2 | 2/2004 | Archer et al. |
| 6,692,315 B1 | 2/2004 | Soumillion et al. |
| 6,694,162 B2 | 2/2004 | Hartlep |
| 6,694,163 B1 | 2/2004 | Vining |
| 6,708,096 B1 | 3/2004 | Frei et al. |
| 6,741,892 B1 | 5/2004 | Meadows et al. |
| 6,748,098 B1 | 6/2004 | Rosenfeld |
| 6,748,276 B1 | 6/2004 | Daignault, Jr. et al. |
| 6,778,846 B1 | 8/2004 | Martinez et al. |
| 6,788,969 B2 | 9/2004 | Dupree et al. |
| 6,795,737 B2 | 9/2004 | Gielen et al. |
| 6,827,681 B2 | 12/2004 | Tanner et al. |
| 6,830,544 B2 | 12/2004 | Tanner |
| 6,845,267 B2 | 1/2005 | Harrison et al. |
| 6,850,802 B2 | 2/2005 | Holsheimer |
| 6,895,280 B2 | 5/2005 | Meadows et al. |
| 6,909,913 B2 | 6/2005 | Vining |
| 6,937,891 B2 | 8/2005 | Leinders et al. |
| 6,937,903 B2 | 8/2005 | Schuler et al. |
| 6,944,497 B2 | 9/2005 | Stypulkowski |
| 6,944,501 B1 | 9/2005 | Pless |
| 6,950,707 B2 | 9/2005 | Whitehurst |
| 6,969,388 B2 | 11/2005 | Goldman et al. |
| 7,003,349 B1 | 2/2006 | Andersson et al. |
| 7,003,352 B1 | 2/2006 | Whitehurst |
| 7,008,370 B2 | 3/2006 | Tanner et al. |
| 7,008,413 B2 | 3/2006 | Kovach et al. |
| 7,035,690 B2 | 4/2006 | Goetz |
| 7,043,293 B1 | 5/2006 | Baura |
| 7,047,082 B1 | 5/2006 | Schrom et al. |
| 7,047,084 B2 | 5/2006 | Erickson et al. |
| 7,050,857 B2 | 5/2006 | Samuelsson et al. |
| 7,054,692 B1 | 5/2006 | Whitehurst et al. |
| 7,136,518 B2 | 5/2006 | Griffin et al. |
| 7,058,446 B2 | 6/2006 | Schuler et al. |
| 7,082,333 B1 | 7/2006 | Bauhahn et al. |
| 7,107,102 B2 | 9/2006 | Daignault et al. |
| 7,126,000 B2 | 10/2006 | Ogawa et al. |
| 7,127,297 B2 | 10/2006 | Law et al. |
| 7,136,695 B2 | 11/2006 | Pless et al. |
| 7,142,923 B2 | 11/2006 | North et al. |
| 7,146,219 B2 | 12/2006 | Sieracki et al. |

(56) References Cited

U.S. PATENT DOCUMENTS

| | | |
|---|---|---|
| 7,146,223 B1 | 12/2006 | King |
| 7,151,961 B1 | 12/2006 | Whitehurst |
| 7,155,279 B2 | 12/2006 | Whitehurst |
| 7,167,760 B2 | 1/2007 | Dawant et al. |
| 7,177,674 B2 | 2/2007 | Echauz et al. |
| 7,181,286 B2 | 2/2007 | Sieracki et al. |
| 7,184,837 B2 | 2/2007 | Goetz |
| 7,191,014 B2 | 3/2007 | Kobayashi et al. |
| 7,209,787 B2 | 4/2007 | Dilorenzo |
| 7,211,050 B1 | 5/2007 | Caplygin |
| 7,216,000 B2 | 5/2007 | Sieracki et al. |
| 7,217,276 B2 | 5/2007 | Henderson |
| 7,218,968 B2 | 5/2007 | Condie et al. |
| 7,228,179 B2 | 6/2007 | Campen et al. |
| 7,231,254 B2 | 6/2007 | DiLorenzo |
| 7,236,830 B2 | 6/2007 | Gliner |
| 7,239,910 B2 | 7/2007 | Tanner |
| 7,239,916 B2 | 7/2007 | Thompson et al. |
| 7,239,926 B2 | 7/2007 | Goetz |
| 7,242,984 B2 | 7/2007 | DiLorenzo |
| 7,244,150 B1 | 7/2007 | Brase et al. |
| 7,252,090 B2 | 8/2007 | Goetz |
| 7,254,445 B2 | 8/2007 | Law et al. |
| 7,254,446 B1 | 8/2007 | Erickson |
| 7,257,447 B2 | 8/2007 | Cates et al. |
| 7,266,412 B2 | 9/2007 | Stypulkowski |
| 7,294,107 B2 | 11/2007 | Simon et al. |
| 7,295,876 B1 | 11/2007 | Erickson |
| 7,299,096 B2 | 11/2007 | Balzer et al. |
| 7,308,302 B1 | 12/2007 | Schuler et al. |
| 7,313,430 B2 | 12/2007 | Urquhart |
| 7,324,851 B1 | 1/2008 | DiLorenzo |
| 7,346,382 B2 | 3/2008 | McIntyre et al. |
| 7,388,974 B2 | 6/2008 | Yanagita |
| 7,450,997 B1 | 11/2008 | Pianca et al. |
| 7,463,928 B2 | 12/2008 | Lee et al. |
| 7,499,048 B2 | 3/2009 | Sieracki et al. |
| 7,505,615 B2 | 3/2009 | Lee et al. |
| 7,548,786 B2 | 6/2009 | Lee et al. |
| 7,565,199 B2 | 7/2009 | Sheffield et al. |
| 7,603,177 B2 | 10/2009 | Sieracki et al. |
| 7,617,002 B2 | 11/2009 | Goetz |
| 7,623,918 B2 | 11/2009 | Goetz |
| 7,650,184 B2 | 1/2010 | Walter |
| 7,657,319 B2 | 2/2010 | Goetz et al. |
| 7,672,734 B2 | 3/2010 | Anderson et al. |
| 7,676,273 B2 | 3/2010 | Goetz et al. |
| 7,680,526 B2 | 3/2010 | McIntyre et al. |
| 7,734,340 B2 | 6/2010 | De Ridder |
| 7,761,165 B1 | 7/2010 | He et al. |
| 7,783,359 B2 | 8/2010 | Meadows |
| 7,792,590 B1 | 9/2010 | Pianca et al. |
| 7,809,446 B2 | 10/2010 | Meadows |
| 7,826,902 B2 | 11/2010 | Stone et al. |
| 7,848,802 B2 | 12/2010 | Goetz et al. |
| 7,860,548 B2 | 12/2010 | McIntyre et al. |
| 7,904,134 B2 | 3/2011 | McIntyre et al. |
| 7,945,105 B1 | 5/2011 | Jaenisch |
| 7,949,395 B2 | 5/2011 | Kuzma |
| 7,974,706 B2 | 7/2011 | Moffitt et al. |
| 8,000,794 B2 | 8/2011 | Lozano |
| 8,019,439 B2 | 9/2011 | Kuzma et al. |
| 8,175,710 B2 | 5/2012 | He |
| 8,180,601 B2 | 5/2012 | Butson et al. |
| 8,195,300 B2 | 6/2012 | Gliner et al. |
| 8,224,450 B2 | 7/2012 | Brase |
| 8,257,684 B2 | 9/2012 | Covalin et al. |
| 8,262,714 B2 | 9/2012 | Hulvershorn et al. |
| 8,271,094 B1 | 9/2012 | Moffitt et al. |
| 8,280,514 B2 | 10/2012 | Lozano et al. |
| 8,295,944 B2 | 10/2012 | Howard et al. |
| 8,326,433 B2 | 12/2012 | Blum et al. |
| 8,364,278 B2 | 1/2013 | Pianca et al. |
| 8,391,985 B2 | 3/2013 | McDonald |
| 8,429,174 B2 | 4/2013 | Ramani et al. |
| 8,452,415 B2 | 5/2013 | Goetz et al. |
| 8,473,061 B2 | 6/2013 | Moffitt et al. |
| 8,483,237 B2 | 7/2013 | Zimmermann et al. |
| 8,543,189 B2 | 9/2013 | Paitel et al. |
| 8,571,665 B2 | 10/2013 | Moffitt et al. |
| 8,606,360 B2 | 12/2013 | Butson et al. |
| 8,620,452 B2 | 12/2013 | King et al. |
| 8,675,945 B2 | 3/2014 | Barnhorst et al. |
| 8,688,235 B1 | 4/2014 | Pianca et al. |
| 8,792,993 B2 | 7/2014 | Pianca et al. |
| 8,831,731 B2 | 9/2014 | Blum et al. |
| 8,849,632 B2 | 9/2014 | Sparks et al. |
| 8,958,615 B2 | 2/2015 | Blum et al. |
| 9,248,272 B2 | 2/2016 | Romero |
| 2001/0031071 A1 | 10/2001 | Nichols et al. |
| 2002/0032375 A1 | 3/2002 | Bauch et al. |
| 2002/0062143 A1 | 5/2002 | Baudino et al. |
| 2002/0087201 A1 | 7/2002 | Firlik et al. |
| 2002/0099295 A1 | 7/2002 | Gil et al. |
| 2002/0115603 A1 | 8/2002 | Whitehouse |
| 2002/0116030 A1 | 8/2002 | Rezei |
| 2002/0123780 A1 | 9/2002 | Grill et al. |
| 2002/0128694 A1 | 9/2002 | Holsheimer |
| 2002/0151939 A1 | 10/2002 | Rezai |
| 2002/0183607 A1 | 12/2002 | Bauch et al. |
| 2002/0183740 A1 | 12/2002 | Edwards et al. |
| 2002/0183817 A1 | 12/2002 | Van Venrooij et al. |
| 2003/0097159 A1 | 5/2003 | Schiff et al. |
| 2003/0149450 A1 | 8/2003 | Mayberg |
| 2003/0171791 A1 | 9/2003 | KenKnight et al. |
| 2003/0212439 A1 | 11/2003 | Schuler et al. |
| 2004/0034394 A1 | 2/2004 | Woods et al. |
| 2004/0044279 A1 | 3/2004 | Lewin et al. |
| 2004/0044378 A1 | 3/2004 | Holsheimer |
| 2004/0044379 A1 | 3/2004 | Holsheimer |
| 2004/0054297 A1 | 3/2004 | Wingeier et al. |
| 2004/0059395 A1 | 3/2004 | North et al. |
| 2004/0106916 A1 | 6/2004 | Quaid et al. |
| 2004/0133248 A1 | 7/2004 | Frei et al. |
| 2004/0152957 A1 | 8/2004 | Stivoric et al. |
| 2004/0181262 A1 | 9/2004 | Bauhahn |
| 2004/0186532 A1 | 9/2004 | Tadlock |
| 2004/0199216 A1 | 10/2004 | Lee et al. |
| 2004/0267330 A1 | 12/2004 | Lee et al. |
| 2005/0021090 A1 | 1/2005 | Schuler et al. |
| 2005/0033380 A1 | 2/2005 | Tanner et al. |
| 2005/0049649 A1 | 3/2005 | Luders et al. |
| 2005/0060001 A1 | 3/2005 | Singhal et al. |
| 2005/0060009 A1 | 3/2005 | Goetz |
| 2005/0070781 A1 | 3/2005 | Dawant et al. |
| 2005/0075689 A1 | 4/2005 | Toy et al. |
| 2005/0085714 A1 | 4/2005 | Foley et al. |
| 2005/0165294 A1 | 7/2005 | Weiss |
| 2005/0171587 A1 | 8/2005 | Daglow et al. |
| 2005/0228250 A1 | 10/2005 | Bitter et al. |
| 2005/0251061 A1 | 11/2005 | Schuler et al. |
| 2005/0261061 A1 | 11/2005 | Nguyen et al. |
| 2005/0261601 A1 | 11/2005 | Schuler et al. |
| 2005/0261747 A1 | 11/2005 | Schuler et al. |
| 2005/0267347 A1 | 12/2005 | Oster |
| 2005/0288732 A1 | 12/2005 | Schuler et al. |
| 2006/0004422 A1 | 1/2006 | De Ridder |
| 2006/0017749 A1 | 1/2006 | McIntyre et al. |
| 2006/0020292 A1 | 1/2006 | Goetz et al. |
| 2006/0069415 A1 | 3/2006 | Cameron et al. |
| 2006/0094951 A1 | 5/2006 | Dean et al. |
| 2006/0095088 A1 | 5/2006 | De Riddler |
| 2006/0155340 A1 | 7/2006 | Schuler et al. |
| 2006/0206169 A1 | 9/2006 | Schuler |
| 2006/0218007 A1 | 9/2006 | Bjorner et al. |
| 2006/0224189 A1 | 10/2006 | Schuler et al. |
| 2006/0235472 A1 | 10/2006 | Goetz et al. |
| 2006/0259079 A1 | 11/2006 | King |
| 2006/0259099 A1 | 11/2006 | Goetz et al. |
| 2007/0000372 A1 | 1/2007 | Rezai et al. |
| 2007/0017749 A1 | 1/2007 | Dold et al. |
| 2007/0027514 A1 | 2/2007 | Gerber |
| 2007/0043268 A1 | 2/2007 | Russell |
| 2007/0049817 A1 | 3/2007 | Preiss et al. |

(56) References Cited

U.S. PATENT DOCUMENTS

| | | |
|---|---|---|
| 2007/0067003 A1 | 3/2007 | Sanchez et al. |
| 2007/0078498 A1 | 4/2007 | Rezai et al. |
| 2007/0083104 A1 | 4/2007 | Butson et al. |
| 2007/0123953 A1 | 5/2007 | Lee et al. |
| 2007/0129769 A1 | 6/2007 | Bourget et al. |
| 2007/0135855 A1 | 6/2007 | Foshee et al. |
| 2007/0150036 A1 | 6/2007 | Anderson |
| 2007/0156186 A1 | 7/2007 | Lee et al. |
| 2007/0162086 A1 | 7/2007 | DiLorenzo |
| 2007/0162235 A1 | 7/2007 | Zhan et al. |
| 2007/0168004 A1 | 7/2007 | Walter |
| 2007/0168007 A1 | 7/2007 | Kuzma et al. |
| 2007/0185544 A1 | 8/2007 | Dawant et al. |
| 2007/0191887 A1 | 8/2007 | Schuler et al. |
| 2007/0191912 A1 | 8/2007 | Ficher et al. |
| 2007/0197891 A1 | 8/2007 | Shachar et al. |
| 2007/0203450 A1 | 8/2007 | Berry |
| 2007/0203532 A1 | 8/2007 | Tass et al. |
| 2007/0203537 A1 | 8/2007 | Goetz et al. |
| 2007/0203538 A1 | 8/2007 | Stone et al. |
| 2007/0203539 A1 | 8/2007 | Stone et al. |
| 2007/0203540 A1 | 8/2007 | Goetz et al. |
| 2007/0203541 A1 | 8/2007 | Goetz et al. |
| 2007/0203543 A1 | 8/2007 | Stone et al. |
| 2007/0203544 A1 | 8/2007 | Goetz et al. |
| 2007/0203545 A1 | 8/2007 | Stone et al. |
| 2007/0203546 A1 | 8/2007 | Stone et al. |
| 2007/0213789 A1 | 9/2007 | Nolan et al. |
| 2007/0213790 A1 | 9/2007 | Nolan et al. |
| 2007/0244519 A1 | 10/2007 | Keacher et al. |
| 2007/0245318 A1 | 10/2007 | Goetz et al. |
| 2007/0255321 A1 | 11/2007 | Gerber et al. |
| 2007/0255322 A1 | 11/2007 | Gerber et al. |
| 2007/0265664 A1 | 11/2007 | Gerber et al. |
| 2007/0276441 A1 | 11/2007 | Goetz |
| 2007/0282189 A1 | 12/2007 | Dan et al. |
| 2007/0288064 A1 | 12/2007 | Butson et al. |
| 2008/0027514 A1 | 1/2008 | DeMulling et al. |
| 2008/0039895 A1 | 2/2008 | Fowler et al. |
| 2008/0071150 A1 | 3/2008 | Miesel et al. |
| 2008/0081982 A1 | 4/2008 | Simon et al. |
| 2008/0086451 A1 | 4/2008 | Torres et al. |
| 2008/0103533 A1 | 5/2008 | Patel et al. |
| 2008/0114233 A1 | 5/2008 | McIntyre et al. |
| 2008/0114579 A1 | 5/2008 | McIntyre et al. |
| 2008/0123922 A1 | 5/2008 | Gielen et al. |
| 2008/0123923 A1 | 5/2008 | Gielen et al. |
| 2008/0133141 A1 | 6/2008 | Frost |
| 2008/0141217 A1 | 6/2008 | Goetz et al. |
| 2008/0154340 A1 | 6/2008 | Goetz et al. |
| 2008/0154341 A1 | 6/2008 | McIntyre et al. |
| 2008/0163097 A1 | 7/2008 | Goetz et al. |
| 2008/0183256 A1 | 7/2008 | Keacher |
| 2008/0188734 A1 | 8/2008 | Suryanarayanan et al. |
| 2008/0215118 A1 | 9/2008 | Goetz et al. |
| 2008/0227139 A1 | 9/2008 | Deisseroth et al. |
| 2008/0242950 A1 | 10/2008 | Jung et al. |
| 2008/0261165 A1 | 10/2008 | Steingart et al. |
| 2008/0269588 A1 | 10/2008 | Csavoy et al. |
| 2008/0300654 A1 | 12/2008 | Lambert et al. |
| 2008/0300797 A1 | 12/2008 | Tabibiazar et al. |
| 2009/0016491 A1 | 1/2009 | Li |
| 2009/0054950 A1 | 2/2009 | Stephens |
| 2009/0082640 A1 | 3/2009 | Kovach et al. |
| 2009/0082829 A1 | 3/2009 | Panken et al. |
| 2009/0112289 A1 | 4/2009 | Lee et al. |
| 2009/0118635 A1 | 5/2009 | Lujan et al. |
| 2009/0118786 A1 | 5/2009 | Meadows et al. |
| 2009/0149917 A1 | 6/2009 | Whitehurst et al. |
| 2009/0187222 A1 | 7/2009 | Barker |
| 2009/0196471 A1 | 8/2009 | Goetz et al. |
| 2009/0196472 A1 | 8/2009 | Goetz et al. |
| 2009/0198306 A1 | 8/2009 | Goetz et al. |
| 2009/0198354 A1 | 8/2009 | Wilson |
| 2009/0204192 A1 | 8/2009 | Carlton et al. |
| 2009/0208073 A1 | 8/2009 | McIntyre et al. |
| 2009/0210208 A1 | 8/2009 | McIntyre et al. |
| 2009/0242399 A1 | 10/2009 | Kamath et al. |
| 2009/0276008 A1 | 11/2009 | Lee et al. |
| 2009/0276021 A1 | 11/2009 | Meadows et al. |
| 2009/0281595 A1 | 11/2009 | King et al. |
| 2009/0281596 A1 | 11/2009 | King et al. |
| 2009/0287271 A1 | 11/2009 | Blum et al. |
| 2009/0287272 A1 | 11/2009 | Kokones et al. |
| 2009/0287273 A1 | 11/2009 | Carlton et al. |
| 2009/0287467 A1 | 11/2009 | Sparks et al. |
| 2009/0299164 A1 | 12/2009 | Singhal et al. |
| 2009/0299165 A1 | 12/2009 | Singhal et al. |
| 2009/0299380 A1 | 12/2009 | Singhal et al. |
| 2010/0010566 A1 | 1/2010 | Thacker et al. |
| 2010/0010646 A1 | 1/2010 | Drew et al. |
| 2010/0023103 A1 | 1/2010 | Elborno |
| 2010/0023130 A1 | 1/2010 | Henry et al. |
| 2010/0030312 A1 | 2/2010 | Shen |
| 2010/0049276 A1 | 2/2010 | Blum et al. |
| 2010/0049280 A1 | 2/2010 | Goetz |
| 2010/0064249 A1 | 3/2010 | Groetken |
| 2010/0076535 A1 | 3/2010 | Pianca et al. |
| 2010/0113959 A1 | 5/2010 | Pascual-Leon et al. |
| 2010/0121409 A1 | 5/2010 | Kothandaraman et al. |
| 2010/0135553 A1 | 6/2010 | Joglekar |
| 2010/0137944 A1 | 6/2010 | Zhu |
| 2010/0152604 A1 | 6/2010 | Kuala et al. |
| 2010/0179562 A1 | 7/2010 | Linker et al. |
| 2010/0268298 A1 | 10/2010 | Moffitt |
| 2010/0324410 A1 | 12/2010 | Paek et al. |
| 2010/0331883 A1 | 12/2010 | Schmitz et al. |
| 2011/0004267 A1 | 1/2011 | Meadows |
| 2011/0005069 A1 | 1/2011 | Pianca |
| 2011/0040351 A1 | 2/2011 | Buston et al. |
| 2011/0066407 A1 | 3/2011 | Butson et al. |
| 2011/0078900 A1 | 4/2011 | Pianca et al. |
| 2011/0130803 A1 | 6/2011 | McDonald |
| 2011/0130816 A1 | 6/2011 | Howard et al. |
| 2011/0130817 A1 | 6/2011 | Chen |
| 2011/0130818 A1 | 6/2011 | Chen |
| 2011/0172737 A1 | 7/2011 | Davis et al. |
| 2011/0184487 A1 | 7/2011 | Alberts et al. |
| 2011/0191275 A1 | 8/2011 | Lujan et al. |
| 2011/0196253 A1 | 8/2011 | McIntyre et al. |
| 2011/0213440 A1 | 9/2011 | Fowler et al. |
| 2011/0238129 A1 | 9/2011 | Moffitt |
| 2011/0306845 A1 | 12/2011 | Osorio |
| 2011/0306846 A1 | 12/2011 | Osorio |
| 2011/0307032 A1 | 12/2011 | Goetz et al. |
| 2011/0313485 A1* | 12/2011 | DeMulling ........ A61N 1/36185 607/45 |
| 2011/0313500 A1 | 12/2011 | Barker et al. |
| 2012/0016378 A1 | 1/2012 | Pianca et al. |
| 2012/0027272 A1 | 2/2012 | Akinyemi et al. |
| 2012/0046710 A1 | 2/2012 | Digiore et al. |
| 2012/0046715 A1 | 2/2012 | Moffitt et al. |
| 2012/0071949 A1 | 3/2012 | Pianca et al. |
| 2012/0078106 A1 | 3/2012 | Dentinger et al. |
| 2012/0089205 A1 | 4/2012 | Boyden et al. |
| 2012/0101552 A1 | 4/2012 | Lazarewicz et al. |
| 2012/0116476 A1 | 5/2012 | Kothandaraman |
| 2012/0165898 A1 | 6/2012 | Moffitt |
| 2012/0165901 A1 | 6/2012 | Zhu et al. |
| 2012/0165911 A1 | 6/2012 | Pianca |
| 2012/0197375 A1 | 8/2012 | Pianca et al. |
| 2012/0203316 A1 | 8/2012 | Moffitt et al. |
| 2012/0203320 A1 | 8/2012 | Digiore et al. |
| 2012/0203321 A1 | 8/2012 | Moffitt et al. |
| 2012/0207378 A1 | 8/2012 | Gupta et al. |
| 2012/0226138 A1 | 9/2012 | DeSalles et al. |
| 2012/0229468 A1 | 9/2012 | Lee et al. |
| 2012/0265262 A1 | 10/2012 | Osorio |
| 2012/0265268 A1 | 10/2012 | Blum et al. |
| 2012/0302912 A1 | 11/2012 | Moffitt et al. |
| 2012/0303087 A1 | 11/2012 | Moffitt et al. |
| 2012/0314924 A1 | 12/2012 | Carlton et al. |
| 2012/0316615 A1 | 12/2012 | Digiore et al. |
| 2012/0316619 A1 | 12/2012 | Goetz et al. |

(56) References Cited

U.S. PATENT DOCUMENTS

| | | |
|---|---|---|
| 2012/0330622 A1 | 12/2012 | Butson et al. |
| 2013/0039550 A1 | 2/2013 | Blum et al. |
| 2013/0060305 A1 | 3/2013 | Bokil |
| 2013/0105071 A1 | 5/2013 | Digiore et al. |
| 2013/0116744 A1 | 5/2013 | Blum et al. |
| 2013/0116748 A1 | 5/2013 | Bokil et al. |
| 2013/0116749 A1 | 5/2013 | Carlton et al. |
| 2013/0116929 A1 | 5/2013 | Carlton et al. |
| 2013/0150922 A1 | 6/2013 | Butson et al. |
| 2013/0197424 A1 | 8/2013 | Bedenbaugh |
| 2013/0197602 A1 | 8/2013 | Pianca et al. |
| 2013/0261684 A1 | 10/2013 | Howard |
| 2013/0289380 A1 | 10/2013 | Molnar et al. |
| 2013/0317587 A1 | 11/2013 | Barker |
| 2013/0325091 A1 | 12/2013 | Pianca et al. |
| 2014/0039587 A1 | 2/2014 | Romero |
| 2014/0066999 A1 | 3/2014 | Carcieri et al. |
| 2014/0067018 A1 | 3/2014 | Carcieri et al. |
| 2014/0067022 A1 | 3/2014 | Carcieri et al. |
| 2014/0122379 A1 | 5/2014 | Moffitt et al. |
| 2014/0277284 A1 | 9/2014 | Chen et al. |
| 2014/0296953 A1 | 10/2014 | Pianca et al. |
| 2014/0343647 A1 | 11/2014 | Romero et al. |
| 2014/0353001 A1 | 12/2014 | Romero et al. |
| 2014/0358207 A1 | 12/2014 | Romero |
| 2014/0358208 A1 | 12/2014 | Howard et al. |
| 2014/0358209 A1 | 12/2014 | Romero et al. |
| 2014/0358210 A1 | 12/2014 | Howard et al. |
| 2015/0018915 A1 | 1/2015 | Leven |
| 2015/0021817 A1 | 1/2015 | Romero et al. |
| 2015/0045864 A1 | 2/2015 | Howard |
| 2015/0051681 A1 | 2/2015 | Hershey |
| 2015/0066111 A1 | 3/2015 | Blum et al. |
| 2015/0066120 A1 | 3/2015 | Govea |
| 2015/0134031 A1 | 5/2015 | Moffitt et al. |
| 2015/0151113 A1 | 6/2015 | Govea et al. |
| 2016/0022995 A1 | 1/2016 | Kothandaraman et al. |
| 2016/0023008 A1 | 1/2016 | Kothandaraman |
| 2016/0030749 A1 | 2/2016 | Carcieri et al. |
| 2016/0096025 A1 | 4/2016 | Moffitt et al. |
| 2016/0136429 A1 | 5/2016 | Massoumi et al. |
| 2016/0136443 A1 | 5/2016 | Kothandaraman et al. |
| 2016/0228692 A1 | 8/2016 | Steinke et al. |
| 2016/0256693 A1 | 9/2016 | Parramon |
| 2016/0375248 A1 | 12/2016 | Carcieri et al. |
| 2016/0375258 A1 | 12/2016 | Steinke |
| 2017/0100593 A1 | 4/2017 | Zottola |
| 2017/0252570 A1 | 9/2017 | Serrano Carmona et al. |

FOREIGN PATENT DOCUMENTS

| | | |
|---|---|---|
| EP | 1372780 | 1/2004 |
| EP | 1559369 | 8/2005 |
| WO | 97/39797 | 10/1997 |
| WO | 98/48880 | 11/1998 |
| WO | 01/90876 | 11/2001 |
| WO | 02/26314 | 4/2002 |
| WO | 02/28473 | 4/2002 |
| WO | 02/065896 | 8/2002 |
| WO | 02/072192 | 9/2002 |
| WO | 03/086185 | 10/2003 |
| WO | 2004/019799 A2 | 3/2004 |
| WO | 2004041080 | 5/2005 |
| WO | 2006017053 | 2/2006 |
| WO | 2006113305 | 10/2006 |
| WO | 20071097859 | 8/2007 |
| WO | 20071097861 A1 | 8/2007 |
| WO | 2007/100427 | 9/2007 |
| WO | 2007/100428 | 9/2007 |
| WO | 2007/112061 | 10/2007 |
| WO | 2009097224 | 8/2009 |
| WO | 2010/120823 A2 | 10/2010 |
| WO | 2011025865 | 3/2011 |
| WO | 2011/139779 A1 | 11/2011 |
| WO | 2011/159688 A2 | 12/2011 |
| WO | 2012088482 | 6/2012 |

OTHER PUBLICATIONS

Obeso, J. A., et al., "Deep-brain stimulation of the subthalamic nucleus or the pars interna of the globus pallidus in Parkinson's disease.", N Engl J Med., 345{131. The Deep-Brain Stimulation for Parkinson's Disease Study Group, (Sep. 27, 2001 ),956-63.

Butson et al.. "Current Steering to control the volume of tissue activated during deep brain stimulation," vol. 1, No. 1, Dec. 3, 2007, pp. 7-15.

Patrick, S. K., et al., "Quantification of the UPDRS rigidity scale", IEEE Transactions on Neural Systems and Rehabilitation Engineering, [see also IEEE Trans. on Rehabilitation Engineering 9(1). (2001),31-41.

Phillips. M. D., et al., "Parkinson disease: pattern of functional MR imaging activation during deep brain stimulation of subthalamic nucleus—initial experience", Radiology 239(1). (Apr. 2006),209-16.

Ericsson, A. et al., "Construction of a patient-specific atlas of the brain: Application to normal aging," Biomedical Imaging: From Nano to Macro, ISBI 2008, 5th IEEE International Symposium, May 14, 2008, pp. 480-483.

Kaikai Shen et al., "Atlas selection strategy using least angle regression in multi-atlas segmentation propagation," Biomedical Imaging: From Nano to Macro, 2011, 8th IEEE International Symposium, ISBI 2011, Mar. 30, 2011, pp. 1746-1749.

Liliane Ramus et al., "Assessing selection methods in the cotnext of multi-atlas based segmentation," Biomedical Imaging: From Nano to Macro, 2010, IEEE International Symposium, Apr. 14, 2010, pp. 1321-1324.

Olivier Commowick et al., "Using Frankenstein's Creature Paradigm to Build a Patient Specific Atlas," Sep. 20, 2009, Medical Image Computing and Computer-Assisted Intervention, pp. 993-1000.

Lotjonen J.M.P. et al., "Fast and robust multi-atlas segmentation of brain magnetic resonance images," NeuroImage, Academic Press, vol. 49, No. 3, Feb. 1, 2010, pp. 2352-2365.

McIntyre, C. C., et al., "How does deep brain stimulation work? Present understanding and future questions.", J Clin Neurophysiol. 21 (1 ). (Jan.-Feb. 2004 ),40-50.

Sanchez Castro et al., "A cross validation study of deep brain stimulation targeting: From experts to Atlas-Based, Segmentation-Based and Automatic Registration Algorithms," IEEE Transactions on Medical Imaging, vol. 25, No. 11, Nov. 1, 2006, pp. 1440-1450.

Plaha, P. , et al., "Stimulation of the caudal zone incerta is superior to stimulation of the subthalamic nucleus in improving contralateral parkinsonism.", Brain 129{Pt 7) (Jul. 2006), 1732-4 7.

Rattay, F, "Analysis of models for external stimulation of axons", IEEE Trans. Biomed. Eng. vol. 33 (1986),974-977.

Rattay, F., "Analysis of the electrical excitation of CNS neurons", IEEE Transactions on Biomedical Engineering 45 (6). (Jun. 1998),766-772.

Rose, T. L., et al., "Electrical stimulation with Pt electrodes. VIII. Electrochemically safe charge injection limits with 0.2 ms pulses [neuronal application]", IEEE Transactions on Biomedical Engineering, 37(11 }, (Nov. 1990), 1118-1120.

Rubinstein, J. T., et al., "Signal coding in cochlear implants: exploiting stochastic effects of electrical stimulation", Ann Otol Rhinol Laryngol Suppl.. 191, (Sep. 2003), 14-9.

Schwan, H.P., et al., "The conductivity of living tissues.", Ann NY Acad Sci., 65(6). (AUQ., 1957),1007-13.

Taylor, R. S., et al., "Spinal cord stimulation for chronic back and leg pain and failed back surgery syndrome: a systematic review and analysis of prognostic factors", Spine 30(1 ). (Jan. 1, 2005), 152-60.

Siegel, Ralph M. et al., "Spatiotemporal dynamics of the functual architecture for gain fields in inferior parietal lobule of behaving monkey," Cerebral Cortex, New York, NY, vol. 17, No. 2, Feb. 2007, pp. 378-390.

(56) References Cited

OTHER PUBLICATIONS

Klein, A. et al., "Evaluation of 14 nonlinear deformation algorithms applied to human brain MRI registration," NeuroImage, Academic Press, Orlando, FL, vol. 46, No. 3, Jul. 2009, pp. 786-802.
Geddes, L. A., et al., "The specific resistance of biological material—a compendium of data for the biomedical engineer and physiologist.", Med Biol Ena. 5(3). (May 1967),271-93.
Gimsa, J., et al., "Choosing electrodes for deep brain stimulation experiments-electrochemical considerations.", J Neurosci Methods, 142(2), (Mar. 30, 20050,251-65.
Vidailhet, M., et al., "Bilateral deep-brain stimulation of the globus pallidus in primary generalized dystonia", N Engl J Med. 352(5) (Feb. 3, 2005),459-67.
Izad, Oliver, "Computationally Efficient Method in Predicating Axonal Excitation," Disseration for Master Degree, Department of Biomedical Engineering, Case Western Reserve University, May 2009.
Jaccard, Paul, "Elude comparative de la distribution florale dans une portion odes Aples et des Jura," Bulletin de la Societe Vaudoise des Sciences Naturelles (1901), 37:547-579.
Dice, Lee R., "Measures of the Amount of Ecologic Association Between Speciesm" Ecology 26(3) (1945): 297-302. doi: 10.2307/1932409, http://jstor.org/stable/1932409.
Rand, WM., "Objective criteria for the evaluation of clustering methods," Journal of the American Statistical Association (American Statistical Association) 66 (336) (1971 ): 846-850, doi:10.2307/2284239, http://jstor.org/stable/2284239.
Hubert, Lawrence et al., "Comparing partitions," Journal of Classification 2(1) (1985): 193-218, doi:10.1007/ BF01908075.
Cover, T.M. et al., "Elements of information theory," (1991) John Wiley & Sons, New York, NY.
Melia, Marina, "Comparing Clusterings by the Variation of Information," Learning Theory and Kernel Machines (2003): 173-187.
Viola, P., et al., "Alignment by maximization of mutual information", International Journal of Com outer Vision 24(2). ( 1997), 137-154.
Butson et al. "StimExplorer: Deep Brain Stimulation Parameter Selection Software System," Acta Neurochirugica, Jan. 1, 2007, vol. 97, No. 2, pp. 569-574.
Butson et al. "Role of Electrode Design on the Volume of Tissue Activated During Deep Brain Stimulation," Journal of Neural Engineering, Mar. 1, 2006, vol. 3, No. 1, pp. 1-8.
Volkmann et al., Introduction to the Programming of Deep Brain Stimulators, Movement Disorders, vol. 17, Suppl. 3, pp. S181-S187 (2002).
Miocinovic et al. "Cicerone: Stereotactic Neurophysiological Recording and Deep Brain Stimulation Electrode Placement Software System," Acta Neurochirurgica Suppl., Jan. 1, 2007, vol. 97, No. 2, pp. 561-567.
Schmidt et al. "Sketching and Composing Widgets for 3D Manipulation," Eurographics, Apr. 2008, vol. 27, No. 2, pp. 301-310.
Volkmann, J., et al., "Basic algorithms for the programming of deep brain stimulation in Parkinson's disease", Mov Disord., 21 Suppl 14. (Jun. 2006),S284-9.
Walter, B. L., et al., "Surgical treatment for Parkinson's disease", Lancet Neural. 3(12). (Dec. 2004),719-28.
Wei, X. F., et al., "Current density distributions, field distributions and impedance analysis of segmented deep brain stimulation electrodes", J Neural Eng .. 2(4). (Dec. 2005), 139-47.
Zonenshayn, M., et al., "Location of the active contact within the subthalamic nucleus (STN) in the treatment of idiopathic Parkinson's disease.", Surg Neurol., 62(3) (Sep. 2004),216-25.
Da Silva et al (A primer on diffusion tensor imaging of anatomical substructures. Neurosurg Focus 15(1): p. 1-4, Article 4, 2003.)
Micheli-Tzanakou, E., et al., "Computational Intelligence for target assesment in Parkinson's disease", Proceedings of SPIE vol. 4479. Applications and Science of Neural Networks, Fuzzy Systems, and Evolutionary Computation IV,(2001),54-69.

Grill, W. M., "Stimulus waveforms for selective neural stimulation", IEEE Engineering in Medicine and Biology Magazine, 14(4}; (Jul.-Aug. 1995), 375-385.
Miocinovic, S., et al., "Sensitivity of temporal excitation properties to the neuronal element activated by extracellular stimulation", J Neurosci Methods. 132(1). (Jan. 15, 2004), 91-9.
Hunka, K. et al., Nursing Time to Program and Assess Deep Brain Stimulators in Movement Disorder Patients, J. Neursci Nurs., 37: 204-10 (Aug. 2005).
Moss, J., et al., "Electron microscopy of tissue adherent to explanted electrodes in dystonia and Parkinson's disease", Brain, 127{Pt 12). (Dec. 2004 ),2755-63.
Montgomery, E. B., et al., "Mechanisms of deep brain stimulation and future technical developments.", Neurol Res. 22(3). 22(3). (Apr. 2000),259-66.
Merrill, D. R., et al., "Electrical stimulation of excitable tissue: design of efficacious and safe protocols", J Neurosci Methods. 141(2), (Feb. 15, 2005), 171-98.
Fisekovic et al., "New Controller for Functional Electrical Stimulation Systems", Med. Eng. Phys. 2001; 23:391-399.
Zhang, Y., et al., "Atlas-guided tract reconstruction for automated and comprehensive examination of the white matter anatomy," Neuroimage 52(4) (2010), pp. 1289-1301.
""BioPSE" The Biomedical Problem Solving Environment", htt12:// www.sci.utah.edu/cibc/software/index.html, MCRR Center for Integrative Biomedical Computing,(2004).
Andrews, R. J., "Neuroprotection trek—the next generation: neuromodulation I. Techniques—deep brain stimulation, vagus nerve stimulation, and transcranial magnetic stimulation.", Ann NY Acad Sci. 993. (May 2003),1-13.
Carnevale, N.T. et al., "The Neuron Book," Cambridge, UK: Cambridge University Press (2006), 480 pages.
Chaturvedi: "Development of Accurate Computational Models for Patient-Specific Deep Brain Stimulation," Electronic Thesis or Dissertation, Jan. 2012, 162 pages.
Chaturvedi, A. et al.: "Patient-specific models of deep brain stimulation: Influence of field model complexity on neural activation predictions," Brain Stimulation, Elsevier, Amsterdam, NL, vol. 3, No. 2 Apr. 2010, pp. 65-77.
Frankemolle, et al., "Reversing cognitive-motor impairments in Parkinson's disease patients using a computational modeling approach to deep brain stimulation programming," Brian 133 (2010), pp. 746-761.
McIntyre, C.C., et al., "Modeling the excitablitity of mammalian nerve fibers: influence of afterpotentials on the recovery cycle," J Neurophysiol, 87(2) (Feb. 2002), pp. 995-1006.
Peterson, et al., "Predicting myelinated axon activation using spatial characteristics of the extracellular field," Journal of Neural Engineering, 8 (2011), 12 pages.
Warman, et al., "Modeling the Effects of Electric Fields on nerver Fibers; Dermination of Excitation Thresholds,"IEEE Transactions on Biomedical Engineering, vol. 39, No. 12 (Dec. 1992), pp. 1244-1254.
Wesselink, et al., "Analysis of Current Density and Related Parameters in Spinal Cord Stimulation," IEEE Transactions on Rehabilitation Engineering, vol. 6, No. 2 Jun. 1998, pp. 200-207.
Andrews, R. J., "Neuroprotection trek—the next generation: neuromodulation II. Applications—epilepsy, nerve regeneration, neurotrophins.", Ann NY Acad Sci. 993 (May 2003), 14-24.
Astrom, M., et al., "The effect of cystic cavities on deep brain stimulation in the basal ganglia: a simulation-based study", J Neural Eng., 3(2), (Jun. 2006).132-8.
Bazin et al., "Free Software Tools for Atlas-based Volumetric Neuroimage Analysis", Proc. SPIE 5747, Medical Imaging 2005: Image Processing, 1824 May 5, 2005.
Back, C., et al., "Postoperative Monitoring of the Electrical Properties of Tissue and Electrodes in Deep Brain Stimulation", Neuromodulation, 6(4), (Oct. 2003 ),248-253.
Baker, K. B., et al., "Evaluation of specific absorption rate as a dosimeter of MRI-related implant heating", J Magn Reson Imaging., 20(2), (Aug. 2004),315-20.
Brown, J. " Motor Cortex Stimulation," Neurosurgical Focus ( Sep. 15, 2001) 11(3):E5.

(56) References Cited

OTHER PUBLICATIONS

Budai et al., "Endogenous Opioid Peptides Acting at m-Opioid Receptors in the Dorsal Horn Contribute to Midbrain Modulation of Spinal Nociceptive Neurons," Journal of Neurophysiology (1998) 79(2): 677-687.
Cesselin, F. "Opioid and anti-opioid peptides," Fundamental and Clinical Pharmacology (1995) 9(5): 409-33 (Abstract only).
Rezai et al., "Deep Brain Stimulation for Chronic Pain" Surgical Management of Pain, Chapter 44 pp. 565-576 (2002).
Xu, MD., SHI-ANG, article entitled "Comparison of Half-Band and Full-Band Electrodes for Intracochlear Electrical Stimulation", Annals of Otology, Rhinology & Laryngology (Annals of Head & Neck Medicine & Surgery), vol. 102 (5) pp. 363-367 May 1993.
Bedard, C. , et al., "Modeling extracellular field potentials and the frequency-filtering properties of extracellular space", Biophys J .. 86(3). (Mar. 2004),1829-42.
Benabid, A. L., et al., "Future prospects of brain stimulation", Neural Res.;22(3), (Apr. 2000),237-46.
Brummer, S. B., et al., "Electrical Stimulation with Pt Electrodes: II—Estimation of Maximum Surface Redox (Theoretical Non-Gassing) Limits", IEEE Transactions on Biomedical Engineering, vol. BME-24, Issue 5, (Sep. 1977),440-443.
Butson, Christopher R., et al., "Deep Brain Stimulation of the Subthalamic Nucleus: Model-Based Analysis of the Effects of Electrode Capacitance on the Volume of Activation", Proceedings of the 2nd International IEEE EMBS, (Mar. 16-19, 2005),196-197.
Mcintyre. Cameron C., et al., "Cellular effects of deep brain stimulation: model-based analysis of activation and inhibition," J Neurophysiol, 91(4) (Apr. 2004), pp. 1457-1469.
Chaturvedi, A., et al., "Subthalamic Nucleus Deep Brain Stimulation: Accurate Axonal Threshold Prediction with Diffusion Tensor Based Electric Field Models", Engineering in Medicine and Biology Society, 2006. EMBS' 06 28th Annual International Conference of the IEEE, IEEE, Piscataway, NJ USA, Aug. 30, 2006.
Butson, Christopher et al., "Predicting the Effects of Deep Brain Stimulation with Diffusion Tensor Based Electric Field Models" Jan. 1, 2001, Medical Image Computing and Computer-Assisted Intervention-Mic CAI 2006 Lecture Notes in Computer Science; LNCS, Springer, Berlin, DE.
Butson, C. R., et al., "Deep brainstimulation interactive visualization system", Society for Neuroscience vol. 898.7 (2005).
Hodaie, M., et al., "Chronic anterior thalamus stimulation for intractable epilepsy," Epilepsia, 43(6) (Jun. 2002), pp. 603-608.
Hoekema, R., et al., "Multigrid solution of the potential field in modeling electrical nerve stimulation," Comput Biomed Res., 31(5) (Oct. 1998), pp. 348-362.
Holsheimer, J., et al., "'Identification of the target neuronal elements in electrical deep brain stimulation," Eur J Neurosci., 12(12) (Dec. 2000), pp. 4573-4577.
Jezernik, S., et al., "Neural network classification of nerve activity recorded in a mixed nerve," Neurol Res., 23(5) (Jul. 2001), pp. 429-434.
Jones, DK., et al., "Optimal strategies for measuring diffusion in anisotropic systems by magnetic resonance imaging," Magn. Reson. Med., 42(3) (Sep. 1999), pp. 515-525.
Krack, P., et al., "Postoperative management of subthalamic nucleus stimulation for Parkinson's disease," Mov. Disord., vol. 17(suppl 3) (2002), pp. 188-197.
Le Bihan, D., et al., "Diffusion tensor imaging: concepts and applications," J Magn Reson Imaging, 13(4) (Apr. 2001), pp. 534-546.
Lee, D. C., et al.; "Extracellular electrical stimulation of central neurons: quantitative studies," In: Handbook of neuroprosthetic methods, WE Finn and PG Lopresti (eds) CRC Press (2003), pp. 95-125.
Levy, AL., et al., "An Internet-connected, patient-specific, deformable brain atlas integrated into a surgical navigation system," J Digit Imaging, 10(3 Suppl 1) (Aug. 1997), pp. 231-237.
Liu, Haiying, et al, "Intra-operative MR-guided DBS implantation for treating PD and ET," Proceedings of SPIE vol. 4319, Department of Radiology & Neurosurgery, University of Minnesota, Minneapolis, MN 55455 (2001), pp. 272-276.
Mcintyre, C. C., et al., "Extracellular stimulation of central neurons: influence of stimulus waveform and frequency on neuronal output," J. Neurophysiol., 88(4), (Oct. 2002), pp. 1592-1604.
Mcintyre, C. C., et al., "Microstimulation of spinal motoneurons: a model study," Proceedings of the 19th Annual International Conference of the IEEE Engineering in Medicine and Biology society, vol. 5, (1997), pp. 2032-2034.
Mcintyre, Cameron C., et al., "Model-based Analysis of deep brain stimulation of the thalamus," Proceedings of the Second joint EMBS/BM ES Conference, vol. 3, Annual Fall Meeting of the Biomedical Engineering Society (Cal. No. 02CH37392) IEEEPiscataway, NJ (2002), pp. 2047-2048.
Mcintyre, C. C., et al., "Model-based design of stimulus trains for selective microstimulation of targeted neuronal populations," Proceedings of the 23rd Annual International Conference of the IEEE Engineering in Medicine and Biology Society, vol. 1 (2001), pp. 806-809.
Mcintyre, C. C., et al., Model-based design of stimulus waveforms for selective microstimulation in the central nervous system Proceedings of the First Joint [Engineering in Medicine and Biology, 1999. 21st Annual Conf. and the 1999 Annual FallMeeting of the Biomedical Engineering Soc.] BM ES/EMBS Conference, vol. 1 (1999), p. 384.
Mcintyre, Cameron C., et al., "Modeling the excitability of mammalian nerve fibers: influence of aflerpotentials on the recovery cycle," J Neurophysiol, 87(2) (Feb. 2002), pp. 995-1006.
Mcintyre, Cameron C., et al., "Selective microstimulation of central nervous system neurons," Annals of biomedical engineering, 28(3) (Mar. 2000), pp. 219-233.
Mcintyre, C. C., et al., "Sensitivity analysis of a model of mammalian neural membrane," Biol Cybern., 79(1) (Jul. 1998), pp. 29-37.
Mcintyre, Cameron C., et al., "Uncovering the mechanism(s) of action of deep brain stimulation: activation, inhibition, or both," Clin Neurophysiol, 115(6) (Jun. 2004), pp. 1239-1248.
Mcintyre, Cameron C., et al., "Uncovering the mechanisms of deep brain stimulation for Parkinson's disease through functional imaging, neural recording, and neural modeling," Crit Rev Biomed Eng., 30(4-6) (2002), pp. 249-281.
Mouine et al. "Multi-Strategy and Multi-Algorithm Cochlear Prostheses", Biomed. Sci. Instrument, 2000; 36:233-238.
Butson et al., "Tissue and Electrode Capacitance Reduce Neural Activation Volumes During Deep Brain Stimulation", Clinical Neurophysiology, 116:2490-2500, Oct. 2005.
Butson et al., "Sources and Effects of Electrode Impedance During Deep Brain Stimulation", Clinical Neurophysiology, 117:44 7-454, Dec. 2005.
D'Haese et al., "Computer-Aided Placement of Deep Brain Stimulators: From Planning to Intraoperative Guidance", IEEE Transaction on Medical Imaging, 24:1469-1478, Nov. 2005.
Gross et al., "Electrophysiological Mapping for the Implantation of Deep Brain Stimulation Surgery for Parkinson's Disease and Tremor", Movement Disorders, 21 :S259-S283, Jun. 2006.
Halpern et al., "Brain Shift During Deep Brain Stimulation Surgery for Parkinson's Disease", Stereotact Funct. Neurosurg., 86:37-43, published online Sep. 2007.
Herzog et al., "Most Effective Stimulation Site in Subthalamic Deep Brain Stimulation for Parkinson'Disease", Movement Disorders, 19:1050-1099, published Mar. 2004.
Jeon et al., A Feasibility Study of Optical Coherene Tomography for Guiding Deep Brain Probes, Journal of Neuroscience Methods, 154:96-101, Jun. 2006.
Khan et al., "Assessment of Brain Shift Related to Deep Brain Stimulation Surgery", Sterreotact Funct. Neurosurg., 86:44-53, published online Sep. 2007.
Koop et al., "Improvement in a Quantitative Measure of Bradykinesia After Microelectrode Recording in Patients with Parkinson's Disease During Deep Brain Stimulation Surgery", Movement Disorders, 21 :673-678, published on line Jan. 2006.

(56) References Cited

OTHER PUBLICATIONS

Lemaire et al., "Brain Mapping in Stereotactic Surgery: A Brief Overview from the Probabilistic Targeting to the Patient-Based Anatomic Mapping", NeuroImage, 37:S109-S115, available online Jun. 2007.

Machado et al., "Deep Brain Stimulation for Parkinson's Disease: Surgical Technique and Perioperative Management", Movement Disorders, 21 :S247-S258, Jun. 2006.

Maks et al., "Deep Brain Stimulation Activation Volumes and Their Association with Neurophysiological Mapping and Therapeutic Outcomes", Downloaded from jnnp.bmj.com, pp. 1-21, published online Apr. 2008.

Moran et al., "Real-Time Refinment of Subthalamic Nucleous Targeting Using Bayesian Decision-Making on the Root Mean Square Measure", Movement Disorders, 21: 1425-1431, published online Jun. 2006.

Sakamoto et al., "Homogeneous Fluorescence Assays for RNA Diagnosis by Pyrene-Conjugated 2'-0-Methyloligoribonucleotides", Nucleosides, Nucleotides, and Nucleric Acids, 26:1659-1664, on line publication Oct. 2007.

Winkler et al., The First Evaluation of Brain Shift During Functional Neurosurgery by Deformation Field Analysis, J. Neural. Neurosurg. Psychiatry, 76:1161-1163, Aug. 2005.

Yelnik et al., "A Three-Dimensional, Histological and Deformable Atlas of the Human Basal J Ganglia. I. Atlas Construction Based on Immunohistochemical and MRI Data", NeuroImage, 34:618,-638,Jan. 2007.

Ward, H. E., et al., "Update on deep brain stimulation for neuropsychiatric disorders," Neurobiol Dis 38 (3) (2010), pp. 346-353.

Alberts et al. "Bilateral subthalamic stimulation impairs cognitive-motor performance in Parkinson's disease patients." Brain (2008), 131, 3348-3360, Abstract.

Butson, Christopher R., et al., "Sources and effects of electrode impedance during deep brain stimulation", Clinical Neurophysiology. vol. 117.(2006),447-454.

An, et al., "Prefronlal cortical projections to longitudinal columns in the midbrain periaqueductal gray in macaque monkeys," J Comp Neural 401 (4) (1998), pp. 455-479.

Bulson, C. R., et al., "Tissue and electrode capacitance reduce neural activation volumes during deep brain stimulation," Clinical Neurophysiology, vol. 116 (2005), pp. 2490-2500.

Carmichael, S. T., et al., "Connectional networks within the orbital and medial prefronlal cortex of macaque monkeys," J Comp Neural 371 (2) (1996), pp. 179-207.

Croxson, et al., "Quantitative investigation of connections of the prefronial cortex in the human and macaque using probabilistic diffusion tractography," J Neurosci 25 (39) (2005), pp. 8854-8866.

Frankemolle, et al., "Reversing cognitive-motor impairments in Parkinson's disease patients using a computational modelling approach to deep brain programming," Brain 133 (2010), pp. 746-761.

Freedman, et al. "Subcortical projections of area 25 (subgenual cortex) of the macaque monkey," J Comp Neurol 421 (2) (2000), pp. 172-188.

Giacobbe, et al., "Treatment resistant depression as a failure of brain homeostatic mechanisms: implications for deep brain stimulation," Exp Neural 219 (1) (2009), pp. 44-52.

Goodman, et al., "Deep brain stimulation for intractable obsessive compulsive disorder: pilot study using a blinded, staggered-onset design," Biol Psychiatry 67 (6) (2010), pp. 535-542.

Greenberg, et al., "Deep brain stimulation of the ventral internal capsule/ventral striatum for obsessive-compulsive disorder: worldwide experience," Mol. Psychiatry 15 (1) (2010), pp. 64-79.

Greenberg. et al., "Three-year outcomes in deep brain stimulation for highly resistant obsessive-compulsive disorder," Neuropsychopharmacology 31 (11) (2006), pp. 2384-2393.

Gutman, et al., "A tractography analysis of two deep brain stimulation white matter targets for depression," Biol Psychiatry 65 (4) (2009), pp. 276-282.

Haber, et al., "Reward-related cortical inputs define a large striatal region in primates that interface with associative cortical connections, providing a substrate for incentive-based learning," J Neurosci 26 (32) (2006), pp. 8368-8376.

Haber, et al., "Cognitive and limbic circuits that are affected by deep brain stimulation," Front Biosci 14 (2009), pp. 1823-1834.

Hines, M. L., et al., "The NEURON simulation environment," Neural Comput., 9(6) (Aug. 15, 1997), pp. 1179-1209.

Hua, et al., "Tract probability maps in stereotaxic spaces: analyses of white matter anatomy and tract-specific quantification," Neuroimage 39 (1) (2008), pp. 336-347.

Johansen-Berg, et al., "Anatomical connectivity of the subgenual cingulate region targeted with deep brain stimulation for treatment-resistant depression," Cereb Cortex 18 (6) (2008), pp. 1374-1383.

Kopell, et al., "Deep brain stimulation for psychiatric disorders," J Clin Neurophysiol 21 (1) (2004), pp. 51-67.

Lozano, et al., "Subcallosal cingulate gyrus deep brain stimulation for treatment-resistant depression," Biol Psychiatry 64 (6) (2008), pp. 461-467.

Lujan, et al., "Tracking the mechanisms of deep brain stimulation for neuropsychiatric disorders," Front Biosci 13 (2008), pp. 5892-5904.

Lujan, J.L. et al., "Automated 3-Dimensional Brain Atlas Fitting to Microelectrode Recordings from Deep Brain Stimulation Surgeries," Stereotact. Funel. Neurosurg. 87(2009), pp. 229-240.

Machado. et al., "Functional topography of the ventral striatum and anterior limb of the internal capsule determined by electrical stimulation of awake patients," Clin Neurophysiol 120 (11) (2009), pp. 1941-1948..

Malone, et al., "Deep brain stimulation of the ventral capsule/ventral striatum for treatment-resistant depression," Biol Psychiatry 65 (4) (2009), pp. 267-275.

Mayberg, H. S., et al., "Deep brain stimulation for treatment-resistant depression," Neuron, 45(5) (Mar. 3, 2005), pp. 651-660.

Mayberg, H. S., et al., "Limbic-cortical dysregulation: a proposed model of depression," J Neuropsychiatry Clin Neurosci. 9 (3) (1997), pp. 471-481.

McIntyre,C. C., et al., "Network perspectives on the mechanisms of deep brain stimulation," Neurobiol Dis 38 (3) (2010), pp. 329-337.

Miocinovic, S., et al., "Experimental and theoretical characterization of the voltage distribution generated by deep brain stimulation," Exp Neurol 216 (i) (2009), pp. 166-176.

Nuttin, et al., "Electrical stimulation in anterior limbs of internal capsules in patients with obsessive-compulsive disorder," Lancet 354 (9189) (1999), p. 1526.

Saxena, et al., "Cerebral glucose metabolism in obsessive-compulsive hoarding," Am J Psychiatry. 161 (6) (2004), pp. 1038-1048.

Viola, et al., "Importance-driven focus of attention," IEEE Trans Vis Comput Graph 12 (5) (2006), pp. 933-940.

Wakana, S., et al., "Reproducibility of quantitative tractography methods applied to cerebral white matter," Neuroimage 36 (3) (2007), pp. 630-644.

Mayr et al., "Basic Design and Construction of the Vienna FES Implants: Existing Solutions and Prospects for New Generations of Implants", Medical Engineering & Physics, 2001; 23:53-60.

Alo, K. M., et al., "New trends in neuromodulation for the management of neuropathic pain," Neurosurgery, 50(4), (Apr. 2002), pp. 690-703; discussion pp. 703-704.

Ashby, P., et al., "Neurophysiological effects of stimulation through electrodes in the human subthalamic nucleus," Brain, 122 (PI 10), (Oct. 1999), pp. 1919-1931.

Baker, K. B., et al., "Subthalamic nucleus deep brain stimulus evoked potentials: Physiological and therapeutic implications," Movement Disorders, 17(5), (Sep./Ocl. 2002), pp. 969-983.

Bammer, R, et al., "Diffusion tensor imaging using single-shot SENSE-EPI", Magn Reson Med., 48(1 ), (Jul. 2002), pp. 128-136.

Basser, P J., et al., "MR diffusion tensor spectroscopy and imaging," Biophys J., 66(1 ), (Jan. 1994), pp. 259-267.

Basser, P J., et al., "New currents in electrical stimulation of excitable tissues," Annu Rev Biomed Eng., 2, (2000), pp. 377-397.

(56) References Cited

OTHER PUBLICATIONS

Benabid, AL., et al., "Chronic electrical stimulation of the ventralis intermedius nucleus of the thalamus as a treatment of movement disorders," J. Neurosurg., 84(2), (Feb. 1996), pp. 203-214.
Benabid, AL., et al., "Combined (Ihalamotoy and stimulation) stereotactic surgery of the VIM thalamic nucleus for bilateral Parkinson disease," Appl Neurophysiol, vol. 50, (1987), pp. 344-346.
Benabid, A L., et al., "Long-term suppression of tremor by chronic stimulation of the ventral intermediate thalamic nucleus," Lancet, 337 (8738), (Feb. 16, 1991 ), pp. 403-406.
Butson, C. R., et al., "Predicting the effects of deep brain stimulation with diffusion tensor based electric field models," Medical Image Computing and Computer-Assisted Intervention—Mic Cai 2006, Lecture Notes in Computer Science (LNCS), vol. 4191, pp. 429-437, LNCS, Springer, Berlin, DE.
Christensen, Gary E., et al., "Volumetric transformation of brain anatomy," IEEE Transactions on Medical Imaging, 16 (6), (Dec. 1997), pp. 864-877.
Cooper, S , et al., "Differential effects of thalamic stimulation parameters on tremor and paresthesias in essential tremor," Movement Disorders, 17(Supp. 5), (2002), p. S193.
Coubes, P. et al., "Treatment of DYT1-generalised dystonia by stimulation of the internal globus pallidus," Lancet, 355 (9222), (Jun. 24, 2000), pp. 2220-2221.
Dasilva, A.F. M., et al., "A Primer Diffusion Tensor Imaging of Anatomical Substructures," Neurosurg. Focus; 15(1) (Jul. 2003), pp. 1-4.
Dawant, B. M., et al., "Compuerized atlas-guided positioning of deep brain stimulators: a feasibility study," Biomedical Image registration, Second International Workshop, WBIR 2003, Revised Papers (Lecture notes in Comput. Sci. vol. (2717), Springer-Verlag Berlin, Germany(2003), pp. 142-150.
Finnis, K. W., et al., "3-D functional atalas of subcortical structures for image guided stereotactic neurosurgery," Neuroimage, vol. 9, No. 6, Iss. 2 (1999), p. S206.
Finnis, K. W., et al., "3D Functional Database of Subcorticol Structures for Surgical Guidance in Image Guided Stereotactic Neurosurgery," Medical Image Computing and Computer-Assisted Intervention—MICCAI'99, Second International Conference. Cambridge, UK, Sep. 19-22, 1999, Proceedings (1999), pp. 758-767.
Finnis, K. W., et al., "A 3-Dimensional Database of Deep Brain Functional Anatomy, and Its Application to Image-Guided Neurosurgery," Proceedings of the Third International Conference on Medical Image Computing and Computer-Assisted Intervention. Lecture Notes in Computer Science; vol. 1935 (2000), pp. 1-8.
Finnis, K. W., et al., "A functional database for guidance of surgical and therapeutic procedures in the deep brain," Proceedings of the 22nd Annual International Conference of the IEEE Engineering in Medicine and Biology Society, vol. 3 (2000), pp. 1787-1789.
Finnis, K. W., et al., "Application of a Population Based Electrophysiological Database to the Planning and Guidance of Deep Brain Stereotactic Neurosurgery," Proceedings of the 5th International Conference on Medical Image Computing I and Computer-Assisted Intervention—Part 11, Lecture Notes in Computer Science; vol. 2489 (2002), pp. 69-76.
Finnis, K. W., et al., "Subcortical physiology deformed into a patient-specific brain atlas for image-guided stereotaxy," Proceedings of SPIE—vol, 4681 Medical Imaging 2002: Visualization, Image-Guided Procedures, and Display (May 2002), pp. 184-195.
Finnis, Krik W., et al., "Three-Dimensional Database of Subcortical Electrophysiology for Image-Guided Stereotatic Functional Neurosurgery," IEEE Transactions on Medical Imaging, 22(1) (Jan. 2003), pp. 93-104.
Gabriels, L , et al., "Deep brain stimulation for treatment-refractory obsessive-compulsive disorder: psychopathological and neuropsychological outcome in three cases," Acta Psychiatr Scand., 107(4) (2003), pp. 275-282.

Gabriels, LA., et al., "Long-term electrical capsular stimulation in patients with obsessive-compulsive disorder," Neurosurgery, 52(6) (Jun. 2003), pp. 1263-1276.
Goodall, E. V. et al., "Modeling study of activation and propagation delays during stimulation of peripheral nerve fibers with a tripolar cuff electrode," IEEE Transactions on Rehabilitation Engineering, [see also IEEE Trans. on Neural Systems and Rehabilitation], 3(3) (Sep. 1995), pp. 272-282.
Goodall, E. V., et al., "Position-selective activation of peripheral nerve fibers with a cuff electrode," IEEE Transactions on Biomedical Engineering, 43(8) (Aug. 1996), pp. 851-856.
Goodall, E. V., "Simulation of activation and propagation delay during tripolar neural stimulation," Proceedings of the 15th Annual International Conference of the IEEE Engineering in Medicine and Biology Society (1993), pp. 1203-1204.
Grill, WM., "Modeling the effects of electric fields on nerve fibers: influence of tissue electrical properties," IEEE Transactions on Biomedical Engineering, 46(8) (1999), pp. 918-928.
Grill, W. M., et al., "Neural and connective tissue response to long-term implantation of multiple contact nerve cuff electrodes," J Biomed Mater Res., 50(2) (May 2000), pp. 215-226.
Grill, W. M., "Neural modeling in neuromuscular and rehabilitation research," Proceedings of the 23rd Annual International Conference of the IEEE Engineering in Medicine and Biology Society, vol. 4 (2001 ), pp. 4065-4068.
Grill, W. M., et al., "Non-invasive measurement of the input-output properties of peripheral nerve stimulating electrodes," Journal of Neuroscience Methods, 65(1) (Mar. 1996), pp. 43-50.
Grill, W. M., et al., "Quantification of recruitment properties of multiple contact cuff electrodes," IEEE Transactions on Rehabilitation Engineering, [see also IEEE Trans. on Neural Systems and Rehabilitation], 4(2) (Jun. 1996), pp. 49-62.
Grill, W. M., "Spatially selective activation of peripheral nerve for neuroprosthetic applications," Ph.D. Case Western Reserve University, (1995), pp. 245 pages.
Grill, W. M., "Stability of the input-output properties of chronically implanted multiple contact nerve cuff stimulating electrodes," IEEE Transactions on Rehabilitation Engineering [see also IEEE Trans. on Neural Systems and Rehabilitation] (1998), pp. 364-373.
Grill, W. M., "Stimulus waveforms for selective neural stimulation," IEEE Engineering in Medicine and Biology Magazine, 14(4) (Jul.-Aug. 1995), pp. 375-385.
Grill, W. M., et al., "Temporal stability of nerve cuff electrode recruitment properties," IEEE 17th Annual Conference Engineering in Medicine and Biology Society, vol. 2 (1995), pp. 1089-1090.
Gross, RE., et al., "Advances in neurostimulation for movement disorders," Neurol Res., 22(3) (Apr. 2000), pp. 247-258.
Guridi et al., "The subthalamic nucleus, hemiballismus and Parkinson's disease: reappraisal of a neurological dogma," Brain, vol. 124, 2001, pp. 5-19.
Haberler, C, et al., "No tissue damage by chronic deep brain stimulation in Parkinson's disease," Ann Neurol., 48(3) (Sep. 2000), pp. 372-376.
Hamel, W, et al., "Deep brain stimulation of the subthalamic nucleus in Parkinson's disease: evaluation of active electrode contacts," J Neurol Neurosurg Psychiatry, 74(8) (Aug. 2003), pp. 1036-1046.
Hanekom, "Modelling encapsulation tissue around cochlear implant electrodes," Med. Biol, Eng. Comput. vol. 43 (2005), pp. 47-55.
Haueisen, J , et al., "The influence of brain tissue anisotropy on human EEG and MEG," Neuroimage, 15(1) (Jan. 2002), pp. 159-166.
D'Haese et al. Medical Image Computing and Computer-Assisted Intervention—MICCAI 2005 Lecture Notes in Computer Science, 2005, vol. 3750, 2005, 427-434.
Rohde et al. IEEE Transactions on Medical Imaging, vol. 22 No. 1 2003 p. 1470-1479.
Dawant et al., Biomedical Image Registration. Lecture Notes in Computer Science, 2003; vol. 2717, 2003, 142-150.
Miocinovic et al., "Stereotactiv Neurosurgical Planning, Recording, and Visualization for Deep Brain Stimulation in Non-Human Primates", Journal of Neuroscience Methods, 162:32-41, Apr. 5, 2007, XP022021469.

(56) References Cited

OTHER PUBLICATIONS

Gemmar et at, "Advanced Methods for Target Navigation Using Microelectrode Recordings in Stereotactic Neurosurgery for Deep Brain Stimulation", 21st IEEE International Symposium on Computer-Based Medical Systems, Jun. 17, 2008, pp. 99-104, XP031284774.
Acar et al., "Safety Anterior Commissure-Posterior Commissure-Based Target Calculation of the Subthalamic Nucleus in Functional Stereotactic Procedures", Stereotactic Funct. Neurosura., 85:287-291, Aug. 2007.
Andrade-Souza, "Comparison of Three Methods of Targeting the Subthalamic Nucleus for Chronic Stimulation in Parkinson's Disease", Neurosurgery, 56:360-368, Apr. 2005.
Anheim et al., "Improvement in Parkinson Disease by Subthalamic Nucleus Stimulation Based on Electrode Placement", Arch Neural., 65:612-616, May 2008.
Mcintyre, Cameron C., et al., "Electric Field and Stimulating Influence generated by Deep Brain Stimulation of the Subthalamaic Nucleus," Clinical Neurophysiology, 115(3) (Mar. 2004), pp. 589-595.
Mcintyre, Cameron C., et al., "Electric field generated by deep brain stimulation of the subthalamic nucleus," Biomedical Engineering Society Annual Meeting, Nashville TN (Oct. 2003), 16 pages.
Mcintyre, Cameron C., et al., "Excitation of central nervous system neurons by nonuniform electric fields," Biophys. J., 76(2) (1999), pp. 878-888.
McNeal, DR., et al., "Analysis of a model for excitation of myelinated nerve," IEEE Trans Biomed Eng., vol. 23 (1976), pp. 329-337.
Micheli-Tzanakou, E. , et al., "Computational Intelligence for target assesment in Parkinson's disease," Proceedings of SPIE vol. 4479, Applications and Science of Neural Networks, Fuzzy Systems, and Evolutionary Computation IV (2001 ), pp. 54-69.
Miocinovic, S., et al., "Computational analysis of subthalamic nucleus and lenticular fasciculus activation during therapeutic deep brain stimulation," J Neurophysiol., 96(3) (Sep. 2006), pp. 1569-1580.
Miranda, P. C., et al., "The distribution of currents inducedin the brain by Magnetic Stimulation: a finite element analysis incorporating OT-MRI-derived conductivity data," Proc. Intl. Soc. Mag. Reson. Med. 9 (2001 ), p. 1540.
Miranda, P. C., et al., "The Electric Field Induced in the Brain by Magnetic Stimulation: A 3-D Finite-Element Analysis of the Effect of Tissue Heterogeneity and Anisotropy," IEEE Transactions on Biomedical Enginering, 50(9) (Sep. 2003), pp. 1074-1085.
Moffitt, MA., et al., "Prediction of myelinated nerve fiber stimulation thresholds: limitations of linear models," IEEE Transactions on Biomedical Engineering, 51 (2) (2003), pp. 229-236.
Moro, E, et al., "The impact on Parkinson's disease of electrical parameter settings in STN stimulation," Neurology, 59 (5) (Sep. 10, 2002), pp. 706-713.
Nowak, LG., et al., "Axons, but not cell bodies, are activated by electrical stimulation in cortical gray matter. I. Evidence from chronaxie measurements," Exp. Brain Res., 118(4) (Feb. 1998), pp. 477-488.
Nowak, LG., et al., "Axons, but not cell bodies, are activated by electrical stimulation in cortical gray matter. II. Evidence from selective inactivation of cell bodies and axon initial segments," Exp. Brain Res., 118(4) (Feb. 1998), pp. 489-500.
O'Suilleabhain, PE., et al., "Tremor response to polarity, voltage, pulsewidth and frequency of thalamic stimulation," Neurology, 60(5) (Mar. 11, 2003), pp. 786-790.
Pierpaoli, C., et al., "Toward a quantitative assessment of diffusion anisotropy," Magn Reson Med., 36(6) (Dec. 1996), pp. 893-906.
Plonsey, R., et al., "Considerations of quasi-stationarity in electrophysiological systems," Bull Math Biophys., 29(4) (Dec. 1967), pp. 657-664.
Ranck, J B., "Specific impedance of rabbit cerebral cortex," Exp. Neurol., vol. 7 (Feb. 1963), pp. 144-152.
Ranck, J B., et al., "The Specific impedance of the dorsal columns of the cat: an anisotropic medium," Exp. Neurol., 11 (Apr. 1965), pp. 451-463.
Ranck, J B., "Which elements are excited in electrical stimulation of mammalian central nervous system: a review," Brain Res., 98(3) (Nov. 21, 1975), pp. 417-440.
Rattay, F., et al al. "A model of the electrically excited human cochlear neuron. I. Contribution of neural substructures to the generation and propagation of spikes," Hear Res., 153(1-2) (Mar. 2001), pp. 43-63.
Rattay, F., "A model of the electrically excited human cochlear neuron. II. Influence of the three-dimensional cochlear structure on neural excitability," Hear Res., 153(1-2) (Mar. 2001), pp. 64-79.
Rattay, F., "Arrival at Functional Electrostimulation by modelling of fiber excitation," Proceedings of the Ninth annual Conference of the IEEE Engineering in Medicine and Biology Society (1987), pp. 1459-1460.
Rattay, F., "The influence of intrinsic noise can preserve the temporal fine structure of speech signals in models of electrically stimulated human cochlear neurones," Journal of Physiology, Scientific Meeting of the Physiological Society, London, England, UK Apr. 19-21, 1999 (Jul. 1999), p. 170P.
Rizzone, M., et al., "Deep brain stimulation of the subthalamic nucleus in Parkinson's disease: effects of variation in stimulation parameters," J. Neurol. Neurosurg. Psychiatry., 71(2) (Aug. 2001), pp. 215-219.
Saint-Cyr, J. A., et al., "Localization of clinically effective stimulating electrodes in the human subthalamic nucleus on magnetic resonance imaging," J. Neurosurg., 87(5) (Nov. 2002), pp. 1152-1166.
Sances, A., et al., "In Electroanesthesia: Biomedical and Biophysical Studies," A Sances and SJ Larson, Eds., Academic Press, NY (1975), pp. 114-124.
SI. Jean, P., et al., "Automated atlas integration and interactive three-dimensional visualization tools for planning and guidance in functional neurosurgery," IEEE Transactions on Medical Imaging, 17(5) (1998), pp. 672-680.
Starr, P.A., et al., "Implantation of deep brain stimulators into the subthalamic nucleus: technical approach and magnetic resonance imaging-verified lead locations," J. Neurosurg., 97(2) (Aug. 2002), pp. 370-387.
Sterio, D., et al., "Neurophysiological refinement of subthalamic nucleus targeting," Neurosurgery, 50(1) (Jan. 2002), pp. 58-69.
Struijk, J. J., et al., "Excitation of dorsal root fibers in spinal cord stimulation: a theoretical study," IEEE Transactions on Biomedical Engineering, 40(7) (Jul. 1993), pp. 632-639.
Struijk, J J., et al., "Recruitment of dorsal column fibers in spinal cord stimulation: influence of collateral branching," IEEE Transactions on Biomedical Engineering, 39(9) (Sep. 1992), pp. 903-912.
Tamma, F., et al.. "Anatomo-clinical correlation of intraoperative stimulation-induced side-effects during HF-DBS of the subthalamic nucleus," Neurol Sci., vol. 23 (Suppl 2) (2002), pp. 109-110.
Tarler, M., et al., "Comparison between monopolar and tripolar configurations in chronically implanted nerve cuff electrodes," IEEE 17th Annual Conference Engineering in Medicine and Biology Society, vol. 2 (1995), pp. 1093-1109.
Testerman, Roy L., "Coritical response to callosal stimulation: A model for determining safe and efficient stimulus parameters," Annals of Biomedical Engineering, 6(4) (1978), pp. 438-452.
Tuch, D.S., et al., "Conductivity mapping of biological tissue using diffusion MRI," Ann NY Acad Sci., 888 (Oct. 30, 1999), pp. 314-316.
Tuch, D.S., et al., "Conductivity tensor mapping of the human brain using diffusion tensor MRI," Proc Nall Acad Sci USA, 98(20) (Sep. 25, 2001), pp. 11697-11701.
Veraart, C., et al, "Selective control of muscle activation with a multipolar nerve cuff electrode," IEEE Transactions on Biomedical Engineering, 40(7) (Jul. 1993), pp. 640-653.
Vercueil, L., et al, "Deep brain stimulation in the treatment of severe dystonia," J. Neurol, 248(8) (Aug. 2001 ), pp. 695-700.
Vilalte, "Circuit Design of the Power-on-Reset," Apr. 2000, pp. 1-25.
Vitek, J. L., "Mechanisms of deep brain stimulation: excitation or inhibition," Mov. Disord., vol. 17 (Suppl. (2002), pp. 69-72.

(56) References Cited

OTHER PUBLICATIONS

Voges, J., et al., "Bilateral high-frequency stimulation in the subthalamic nucleus for the treatment of Parkinson disease: correlation of therapeutic effect with anatomical electrode position," J. Neurosurg., 96(2) (Feb. 2002), pp. 269-279.
Wakana, S., et al., "Fiber tract-based atlas of human white matter anatomy," Radiology, 230(1) (Jan. 2004), pp. 77-87.
Alexander, DC., et al., "Spatial transformations of diffusion tensor magnetic resonance images," IEEE Transactions on Medical Imaging, 20 (11), (2001), pp. 1131-1139.
Wu, Y. R., et al., "Does Stimulation of the GPi control dyskinesia by activating inhibitory axons?," Mov. Disord., vol. 16 (2001), pp. 208-216.
Yelnik, J., et al., "Localization of stimulating electrodes in patients with Parkinson disease by using a three-dimensional atlas-magnetic resonance imaging coregistration method," J Neurosurg., 99(1) (Jul. 2003), pp. 89-99.
Yianni, John, et al., "Globus pallidus internus deep brain stimulation for dystonic conditions: a prospective audit," Mov. Disord., vol. 18 (2003), pp. 436-442.
Zonenshayn, M., et al., "Comparison of anatomic and neurophysiological methods for subthalamic nucleus targeting," Neurosurgery, 47(2) (Aug. 2000), pp. 282-294.
Voghell et al., "Programmable Current Source Dedicated to Implantable Microstimulators" ICM '98 Proceedings of the Tenth International Conference, pp. 67-70.
Butson, Christopher R., et al., "Patient-specific analysis of the volume of tissue activated during deep brain stimulation", NeuroImage. vol. 34. (2007),661-670.
Adler, DE., et al., "The tentorial notch: anatomical variation, morphometric analysis, and classification in 100 human autopsy cases," J. Neurosurg., 96(6), (Jun. 2002), pp. 1103-1112.
Jones et al., "An Advanced Demultiplexing System for Physiological Stimulation", IEEE Transactions on Biomedical Engineering, vol. 44 No. 12 Dec. 1997, pp. 1210-1220.
McIntyre, Cameron , et al., "Finite element analysis of the current-density and electric field generated by metal microelectrodes", Ann Biomed Eng . 29(3), (2001 ),227-235.
Foster, K. R., et al,, "Dielectric properties of tissues and biological materials: a critical review.", Grit Rev Biomed Ena. 17(1 ). {1989),25-104.
Limousin, P., et al., "Electrical stimulation of the subthalamic nucleus in advanced Parkinson's disease", N Engl J Med .. 339(16), (Oct. 15, 1998), 1105-11.
Kitagawa, M., et al., "Two-year follow-up of chronic stimulation of the posterior subthalamic white matter for tremor-dominant Parkinson's disease.", Neurosurgery. 56(2). (Feb. 2005),281-9.
Johnson, M. D., et al., "Repeated voltage biasing improves unit recordings by reducing resistive tissue impedances", IEEE Transactions on Neural Systems and Rehabilitation Engineering, [see also IEEE Trans. on Rehabilitation Engineering (2005), 160-165.
Holsheimer, J. , et al., "Chronaxie calculated from current-duration and voltage-duration data", J Neurosci Methods. 97(1). (Apr. 1, 2000),45-50.
Hines, M. L., et al., "The NEURON simulation environment", Neural Comput. 9(6). (Aug. 15, 1997), 1179-209.
Herzog, J., et al., "Most effective stimulation site in subthalamic deep brain stimulation for Parkinson's disease", Mov Disord. 19(9). (Sep. 2004),1050-4.
Hershey, T., et al., "Cortical and subcortical blood flow effects of subthalamic nucleus stimulation in PD.", Neurology 61(6). (Sep. 23, 2003),816-21.
Hemm, S. , et al., "Evolution of Brain Impedance in Dystonic Patients Treated by GPi Electrical Stimulation", Neuromodulation 7(2) (Apr. 2004),67-75.
Hemm, S., et al., "Deep brain stimulation in movement disorders: stereotactic coregistration of two-dimensional electrical field modeling and magnetic resonance imaging.", J Neurosurg. 103(6): (Dec. 2005),949-55.
Haueisen, J, et al., "The influence of brain tissue anisotropy on human EEG and MEG", Neuroimage 15(1) (Jan. 2002),159-166.
Haslinger, B., et al., "Frequency-correlated decreases of motor cortex activity associated with subthalamic nucleus stimulation in Parkinson's disease.", Neuroimage 28(3). (Nov. 15, 2005),598-606.
Hashimoto, T. , et al., "Stimulation of the subthalamic nucleus changes the firing pattern of pallidal neurons", J Neurosci. 23(5). (Mar. 1, 2003),1916-23.
Hardman, C. D., et al., "Comparison of the basal ganglia in rats, marmosets, macaques, baboons, and humans: volume and neuronal number for the output, internal relay, and striatel modulating nuclei", J Comp Neurol., 445(3). (Apr. 8, 2002),238-55.
McNaughtan et al., "Electrochemical Issues in Impedance Tomography", 1st World Congress on Industrial Process Tomography, Buxton, Greater Manchester, Apr. 14-17, 1999.
Grill, WM., et al., "Electrical properties of implant encapsulation tissue", Ann Biomed Eng. vol. 22. (1994),23-33.
Grill, W. M., et al., "Deep brain stimulation creates an informational lesion of the stimulated nucleus", Neuroreport. 1517t (May 19, 2004 ), 1137-40.
Pulliam CL, Heldman DA, Orcutt TH, Mera TO, Giuffrida JP, Vitek JL. Motion sensor strategies for automated optimization of deep brain stimulation in Parkinson's disease. Parkinsonism Relat Disord. Apr. 2015; 21(4):378-82.

\* cited by examiner

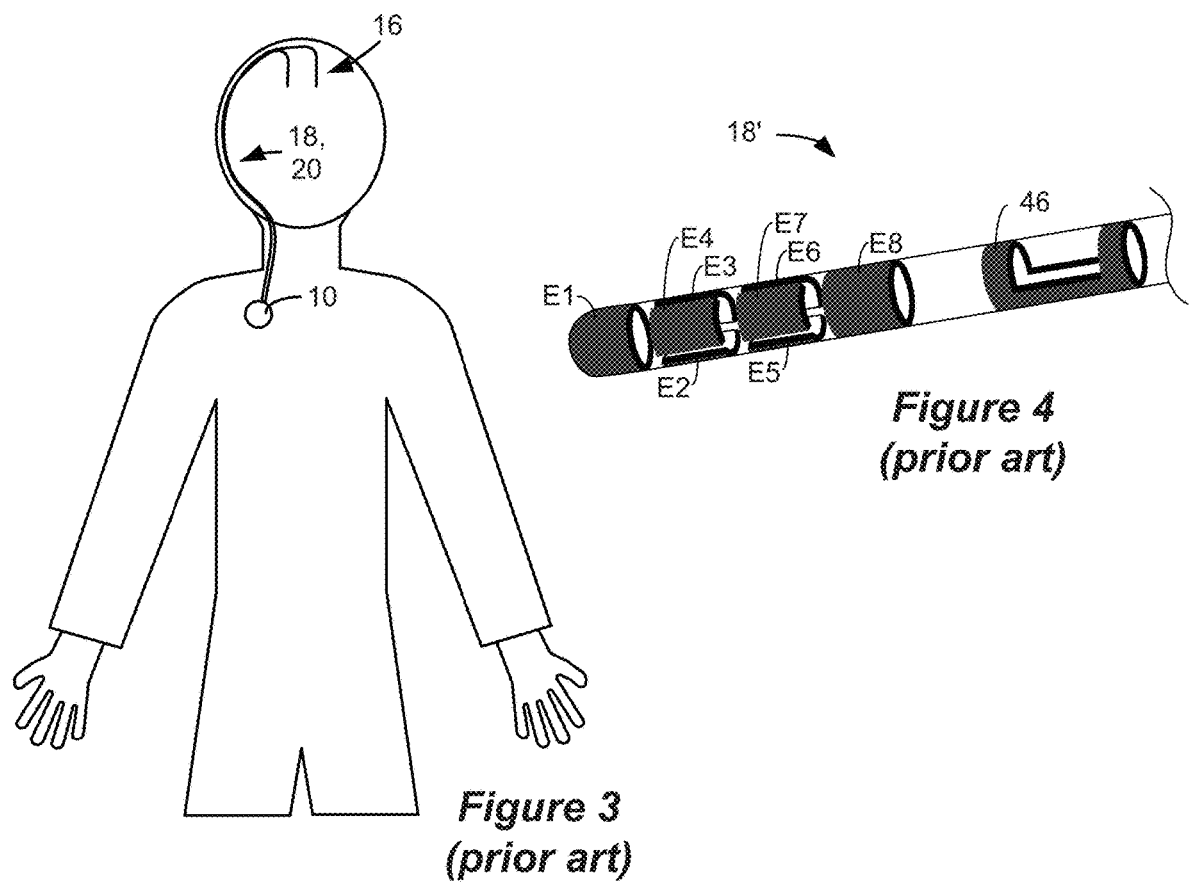
Figure 3
*(prior art)*
Figure 4
*(prior art)*
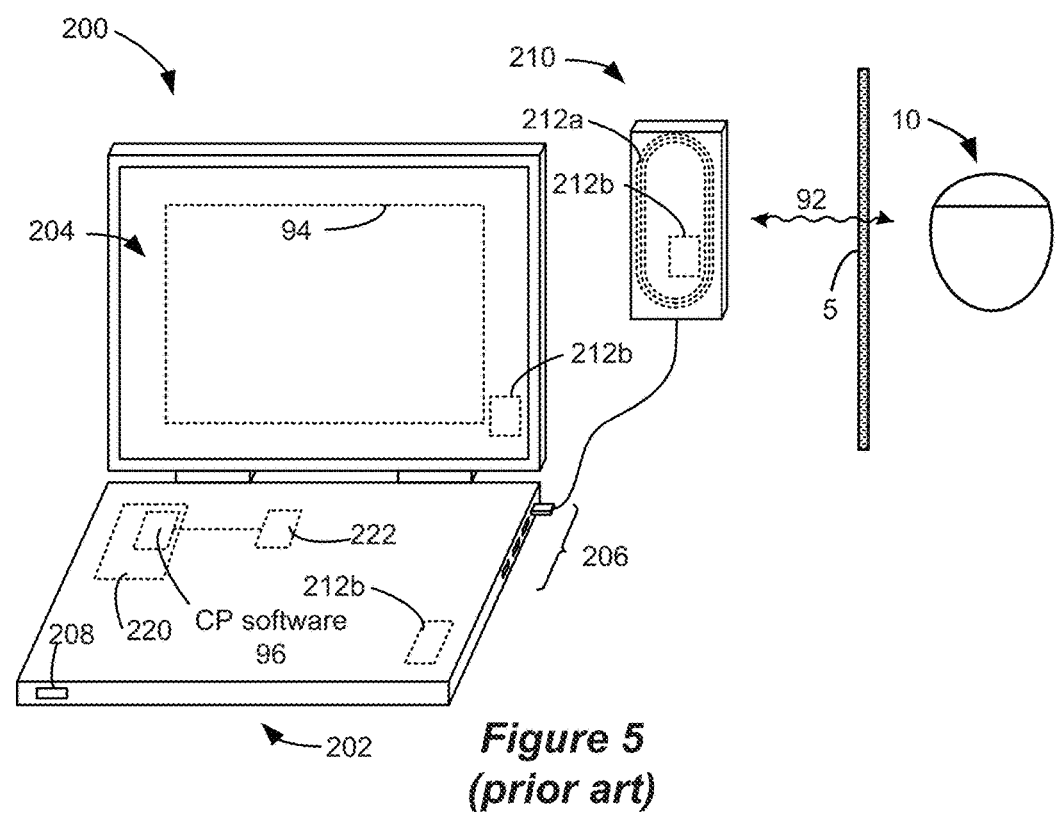
Figure 5
*(prior art)*

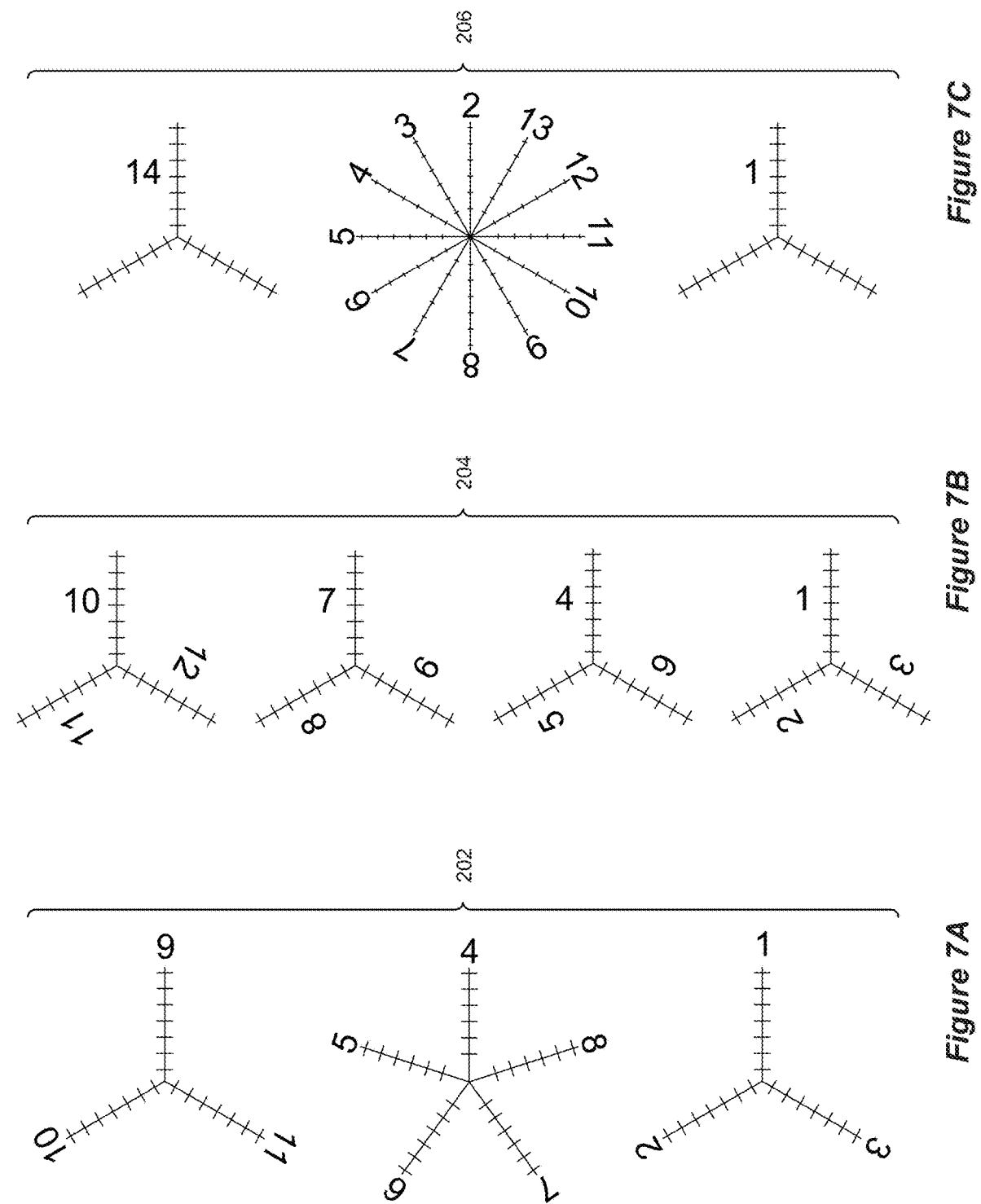

*Figure 11*

| Patient ID | Date | | | | | | | | | | |
|---|---|---|---|---|---|---|---|---|---|---|---|
| Electrode | CF [%] | PW [µs] | Freq [Hz] | Amp [mA] | TE | TE Pos | TE Rating | SE | SE Pos | SE Rating | Notes |
| E1 | 100 | 60 | 130 | | Tremor | Left Hand | 3.0 | | | | Baseline |
| E1 | 100 | 60 | 130 | 1.0 | Tremor | Left Hand | 3.0 | | | | |
| E1 | 100 | 60 | 130 | 2.0 | Tremor | Left Hand | 2.5 | | | | |
| E1 | 100 | 60 | 130 | 3.0 | Tremor | Left Hand | 1.0 | | | | |
| E1 | 100 | 60 | 130 | 3.0 | | | | Paresthesia | Left Hand | 0.5 | |
| E1 | 100 | 60 | 130 | 4.0 | Tremor | Left Hand | 2.0 | | | | |
| E1 | 100 | 60 | 130 | 4.0 | | | | Paresthesia | Left Hand | 1.5 | |
| E1 | 100 | 60 | 130 | 5.0 | Tremor | Left Hand | 3.0 | | | | |
| E1 | 100 | 60 | 130 | 5.0 | | | | Paresthesia | Left Hand | 2.5 | Discomfort |
| E2 | 100 | 60 | 130 | 1.0 | Tremor | Left Hand | 2.5 | | | | |
| E2 | 100 | 60 | 130 | 2.0 | Tremor | Left Hand | 1.5 | | | | |
| E2 | 100 | 60 | 130 | 3.0 | Tremor | Left Hand | 0.5 | | | | |
| E2 | 100 | 60 | 130 | 3.0 | | | | Paresthesia | Left Hand | 0.5 | |
| E2 | 100 | 60 | 130 | 4.0 | Tremor | Left Hand | 0.0 | | | | Eliminated |
| E2 | 100 | 60 | 130 | 4.0 | | | | Paresthesia | Left Hand | 0.5 | |
| E2 | 100 | 60 | 130 | 5.0 | Tremor | Left Hand | 0.5 | | | | |
| E2 | 100 | 60 | 130 | 5.0 | | | | Paresthesia | Left Hand | 1.0 | |
| E234 | 33 | 60 | 130 | 1.0 | Tremor | Left Hand | 3.0 | | | | |
| E234 | 33 | 60 | 130 | 2.0 | Tremor | Left Hand | 2.5 | | | | |
| E234 | 33 | 60 | 130 | 3.0 | Tremor | Left Hand | 2.5 | | | | |
| E234 | 33 | 60 | 130 | 3.0 | | | | Paresthesia | Left Hand | 0.5 | |
| E234 | 33 | 60 | 130 | 4.0 | Tremor | Left Hand | 2.0 | | | | |
| E234 | 33 | 60 | 130 | 4.0 | | | | Paresthesia | Left Hand | 1.0 | |
| E234 | 33 | 60 | 130 | 5.0 | Tremor | Left Hand | 1.5 | | | | |
| E234 | 33 | 60 | 130 | 5.0 | | | | Paresthesia | Left Hand | 1.5 | |

*Figure 13*

VISUALIZATION OF DEEP BRAIN STIMULATION EFFICACY

CROSS-REFERENCE TO RELATED APPLICATIONS

This application claims the benefit under 35 U.S.C. § 119(e) of U.S. Provisional Patent Application Ser. No. 62/471,540, filed Mar. 15, 2017, which is incorporated herein by reference.

FIELD OF THE TECHNOLOGY

The present disclosure relates to techniques that provide an improved visualization of the efficacy of deep brain stimulation settings.

INTRODUCTION

Neurostimulation devices are devices that generate and deliver electrical stimuli to nerves and tissues for the therapy of various biological disorders, such as pacemakers to treat cardiac arrhythmia, defibrillators to treat cardiac fibrillation, cochlear stimulators to treat deafness, retinal stimulators to treat blindness, muscle stimulators to produce coordinated limb movement, spinal cord stimulators to treat chronic pain, cortical and deep brain stimulators to treat motor and psychological disorders, and other neural stimulators to treat urinary incontinence, sleep apnea, shoulder sublaxation, etc. The description that follows focuses on techniques to evaluate the efficacy of the therapy provided by a Deep Brain Stimulation (DBS) system, such as is disclosed in U.S. Patent Application Publication No. 2013/0184794.

As shown in FIG. 1, a DBS system typically includes an implantable pulse generator (IPG) 10, which includes a biocompatible device case 12 that is formed from a metallic material such as titanium. The case 12 typically comprises two components that are welded together, and it holds the circuitry and battery 14 (FIG. 2) necessary for the IPG 10 to function. The battery 14 may be either rechargeable or primary (non-rechargeable) in nature. The IPG 10 is coupled to electrodes 16 via one or more electrode leads 18 (two of which are shown). The proximal ends of the leads 18 include electrode terminals 20 that are coupled to the IPG 10 at one or more connector blocks 22 fixed in a header 24, which can comprise an epoxy for example. Contacts in the connector blocks 22 make electrical contact with the electrode terminals 20, and communicate with the circuitry inside the case 12 via feedthrough pins 26 passing through a hermetic feedthrough 28 to allow such circuitry to provide stimulation to or monitor the various electrodes 16. The feedthrough assembly 28, which is typically a glass, ceramic, or metallic material, is affixed to the case 12 at its edges to form a hermetic seal. In the illustrated system, there are sixteen electrodes 16 split between two leads 18, although the number of leads and electrodes is application specific and therefore can vary.

As shown in FIG. 2, IPG 10 contains a charging coil 30 for wireless charging of the IPG's battery 14 using an external charging device 50, assuming that battery 14 is a rechargeable battery. If IPG 10 has a primary battery 14, charging coil 30 in the IPG 10 and external charger 50 can be eliminated. IPG 10 also contains a telemetry coil antenna 32 for wirelessly communicating data with an external controller device 40, which is explained further below. In other examples, antenna 32 can comprise a short-range RF antenna such as a slot, patch, or wire antenna. IPG 10 also contains control circuitry such as a microcontroller 34, and one or more Application Specific Integrated Circuit (ASICs) 36, which can be as described for example in U.S. Pat. No. 8,768,453. ASIC(s) 36 can include current generation circuitry for providing stimulation pulses at one or more of the electrodes 16 and may also include telemetry modulation and demodulation circuitry for enabling bidirectional wireless communications at antenna 32, battery charging and protection circuitry coupleable to charging coil 30, DC-blocking capacitors in each of the current paths proceeding to the electrodes 16, etc. Components within the case 12 are integrated via a printed circuit board (PCB) 38.

FIG. 2 further shows the external components referenced above, which may be used to communicate with the IPG 10, in plan and cross section views. External controller 40 may be used to control and monitor the IPG 10 via a bidirectional wireless communication link 42 passing through a patient's tissue 5. For example, the external controller 40 may be used to provide or adjust a stimulation program for the IPG 10 to execute that provides stimulation to the patient. The stimulation program may specify a number of stimulation parameters, such as which electrodes are selected for stimulation; whether such active electrodes are to act as anodes or cathodes; and the amplitude (e.g., current), frequency, and duration of stimulation at the active electrodes, assuming such stimulation comprises stimulation pulses as is typical.

Communication on link 42 can occur via magnetic inductive coupling between a coil antenna 44 in the external controller 40 and the IPG 10's telemetry coil 32 as is well known. Typically, the magnetic field comprising link 42 is modulated via Frequency Shift Keying (FSK) or the like, to encode transmitted data. For example, data telemetry via FSK can occur around a center frequency of fc=125 kHz, with a 129 kHz signal representing transmission of a logic '1' bit and 121 kHz representing a logic '0' bit. However, transcutaneous communications on link 42 need not be by magnetic induction, and may comprise short-range RF telemetry (e.g., Bluetooth, WiFi, Zigbee, MICS, etc.) if antennas 44 and 32 and their associated communication circuitry are so configured. The external controller 40 is generally similar to a cell phone and includes a hand-held, portable housing.

External charger 50 provides power to recharge the IPG 10's battery 14 should that battery be rechargeable. Such power transfer occurs by energizing a charging coil 54 in the external charger 50, which produces a magnetic field comprising transcutaneous link 52, which may occur with a different frequency (f2=80 kHz) than data communications on link 42. This magnetic field 52 energizes the charging coil 30 in the IPG 10, which is rectified, filtered, and used to recharge the battery 14. Link 52, like link 42, can be bidirectional to allow the IPG 10 to report status information back to the external charger 50, such as by using Load Shift Keying as is well-known. For example, once circuitry in the IPG 10 detects that the battery 14 is fully charged, it can cause charging coil 30 to signal that fact back to the external charger 50 so that charging can cease. Like the external controller 40, external charger 50 generally comprises a hand-holdable and portable housing.

In a DBS application, as is useful in the treatment of neurological disorders such as Parkinson's disease, the IPG 10 is typically implanted under the patient's clavicle (collarbone), and the leads 18 are tunneled through the neck and between the skull and the scalp where the electrodes 16 are implanted through holes drilled in the skull in the left and right sides of the patient's brain, as shown in FIG. 3. Specifically, the electrodes 16 may be implanted in the subthalamic nucleus (STN), the pedunculopontine nucleus (PPN), or the globus pallidus internus (GPi). Stimulation therapy provided by the IPG 10 has shown promise in reducing the symptoms of neurological disorders, including rigidity, bradykinesia, tremor, gait and turning impairment, postural instability, freezing, arm swing, balance impairment, and dystonia.

While FIG. 1 generically illustrates the electrodes 16 as aligned linearly along a lead 18, electrode leads 18 for DBS applications commonly include segmented electrodes that allow for directional control of stimulation. The electrode lead 18' in FIG. 4 includes multiple circumferential (or ring) electrodes and multiple segmented electrodes. In particular, electrodes 1 and 8 are circumferential electrodes that extend around the circumference of the lead 18' while electrodes 2-7 are segmented electrodes. As used herein, segmented electrodes refer to electrodes that do not extend fully around the perimeter of an electrode lead 18. In the illustrated embodiment, the segmented electrodes are arranged with three electrodes at a particular axial position, each segmented electrode spanning an approximately 110 degree arc around the lead 18' with approximately 10 degree spaces between neighboring segmented electrodes. Although a particular example of a lead is illustrated in FIG. 4, the type and placement of electrodes 16 along a lead is application specific and therefore can vary. For example, a lead may include more or fewer segmented electrodes at a given axial position and more or fewer circumferential electrodes in addition to the segmented electrodes. As will be understood, because the segmented electrodes are separated by a non-conductive break, electrical stimulation that is directed to a segmented electrode propagates outward in the direction of the electrode rather than uniformly about the lead 18 as with circumferential electrodes. The lead 18' additionally includes a marker 46 that is aligned with segmented electrodes 2 and 5. The marker 46 provides a visual indication of the lead's orientation prior to implantation as well as a radiological indication of the lead's orientation after implantation.

After the leads are implanted, a "fitting" procedure is performed in order to customize the parameters of the stimulation provided by the IPG 10 to obtain the greatest benefit for the patient. The IPG 10 can, for example, be programmed with multiple stimulation programs that can each include multiple stimulation routines. Each stimulation routine specifies parameters such as pulse width, stimulation amplitude, frequency, and the electrode(s) that serve as anodes and cathodes. The stimulation routines within a particular program may be executed in succession when the program is active. Moreover, different stimulation programs may be created for different situations. For example, the IPG 10 may be configured with a first program that provides therapy that is effective when the patient is sleeping and a second program that provides therapy that is effective when the patient is awake.

Referring to FIG. 5, the fitting process is typically performed by communicating different stimulation routines from a clinician's programmer system (CP System) 200 to the IPG 10 and observing the patient's responses to the IPG 10's execution of the different routines. For a DBS application, a clinician may observe the extent to which the current stimulation routine decreases the effects of the patient's neurological disorder (e.g., the extent to which the stimulation routine decreases the degree of tremor) as well as any side effects induced as a result of the stimulation routine. As shown, CP system 200 can comprise a computing device 202, such as a desktop, laptop, or notebook computer, a tablet, a mobile smart phone, a Personal Data Assistant (PDA)-type mobile computing device, etc. (hereinafter "CP computer"). In FIG. 5, CP computer 202 is shown as a laptop computer that includes typical computer user interface means such as a screen 204, a mouse, a keyboard, speakers, a stylus, a printer, etc., not all of which are shown for convenience.

Also shown in FIG. 5 is an accessory communication head 210 that is coupleable to a port of the CP computer 202, such as a USB port 206, and that is specific to the CP computer 202+s operation as a neurostimulator controller. Communication between the CP system 200 and the IPG 10 may comprise magnetic inductive or short-range RF telemetry schemes (as described above with respect to communications between the IPG 10 and the programmer 40), and in this regard the IPG 10 and the CP computer 202 and/or the communication head 210 (which can be placed proximate to the IPG 10) may include antennas compliant with the telemetry means chosen. For example, the communication head 210 can include a coil antenna 212a, a short-range RF antenna 212b, or both. The CP computer 202 may also communicate directly with the IPG 10, for example using an integral short-range RF antenna 212b, without the use of the communication head 210.

If the CP system 200 includes a short-range RF antenna (either in CP computer 202 or communication head 210), such antenna can also be used to establish communication between the CP system 200 and other devices, and ultimately to larger communication networks such as the Internet. The CP system 200 can typically also communicate with such other networks via a wired link provided at an Ethernet or network port 208 on the CP computer 202, or with other devices or networks using other wired connections (e.g., at USB ports 206).

To test different stimulation routines during the fitting procedure, the user interfaces with a clinician programmer graphical user interface (CP GUI) 94 provided on the display 204 of the CP computer 202. As one skilled in the art understands, the CP GUI 94 can be rendered by execution of CP software 96 on the CP computer 202, which software may be stored in the CP computer 202's non-volatile memory 220. One skilled in the art will additionally recognize that execution of the CP software 96 in the CP computer 202 can be facilitated by control circuitry 222 such as a microprocessor, microcomputer, an FPGA, other digital logic structures, etc., which is capable of executing programs in a computing device. Such control circuitry 222 when executing the CP software 96 will in addition to rendering the CP GUI 94 cause telemetry circuitry in the CP computer 202 to communicate the stimulation routines to the IPG 10 using a suitable antenna 212a or 212b, either in the communication head 210 or the CP computer 202 as explained earlier. The CP software 96 enables a user to select the type of electrode lead(s) that have been implanted (e.g., from a list of leads that are configured in the software 96) and to customize the stimulation routine using the available electrodes on the implanted lead. In this way, the user can communicate different stimulation routines to the IPG 10 for execution to observe the effects of the various routines and to hone in on the appropriate settings for the patient.

The inventor has observed that existing CP GUIs 94 do not provide a visualization of the efficacy of DB S stimulation applied using an electrode lead having segmented electrodes that enable directional control of applied stimulation, such as the lead 18'. The present disclosure cures this deficiency of existing CP GUIs 94.

SUMMARY

In one aspect, a non-transitory computer-readable medium is disclosed having instructions to cause control circuitry in a computing device to generate a graphical user interface on a display of the computing device that includes a representation of one or more electrode leads that are implantable in a patient's brain, wherein each lead representation comprises a representation of a position of a plurality of segmented electrodes; cause telemetry circuitry in the computing device to communicate a stimulation routine to a neurostimulator that is connected to the one or more electrode leads; receive one or more inputs that are indicative of a patient's response to execution of the stimulation routine by the neurostimulator; and display on the computing device one or more symbols that are indicative of an effectiveness of the stimulation routine, wherein the one or more symbols are based on the received one or more inputs and are displayed at a position on the lead representation that corresponds to parameters of the stimulation routine.

The one or more inputs may include one or more of a type of a symptom of the patient, an anatomical position of the patient's symptom, and a rating of a severity of the patient's symptom. The one or more inputs may additionally or alternatively include one or more of a type of side effect caused by the stimulation routine, an anatomical position of the side effect, and a rating of a severity of the side effect. The graphical user interface may include a field that is configured to receive a baseline rating of a severity of a symptom of the patient when no stimulation is applied. The one or more symbols may include an improvement indicator that is based on a difference between the baseline rating and a rating of a severity of the symptom when the stimulation routine is executed by the neurostimulator, and a color of the improvement indicator may be determined based on the difference between the baseline rating and the rating of the severity of the symptom when the stimulation routine is executed by the neurostimulator. The one or more symbols may additionally or alternatively include a side effect indicator that is based on a severity of one or more side effects caused by the execution of the stimulation routine by the neurostimulator, and a color of the side effect indicator may be determined based on the severity of the one or more side effects caused by the execution of the stimulation routine by the neurostimulator. The improvement indicator may be a circle and the side effect indicator may be a ring around the circle.

Each lead representation may include one or more electrode representations, and at least one of the electrode representations may be a segmented electrode representation that represents a set of the segmented electrodes. Each of the electrode representations may include an origin and one or more spokes that extend outward from the origin, and each spoke of a segmented electrode representation may extend from the origin in a direction that corresponds to a position of one of the segmented electrodes about the electrode lead. The graphical user interface may include at least one orientation adjuster to adjust an orientation of the one or more lead representations to match an orientation in which the one or more electrode leads are implanted in the patient, and the one or more orientation adjusters may rotate the spokes of a lead representation's electrode representations about their origin. Each of the spokes may be a stimulation amplitude axis, and the one or more symbols may be displayed along the one or more axes. The one or more inputs may be user inputs or they may be received from one or more sensors.

In another aspect, a system is disclosed having a neurostimulator and a non-transitory computer-readable medium. The non-transitory computer-readable medium may have instructions to cause control circuitry in a computing device to generate a graphical user interface on a display of the computing device that includes a representation of one or more electrode leads that are connected to the neurostimulator, wherein each lead representation includes a representation of a position of a plurality of segmented electrodes; cause telemetry circuitry in the computing device to communicate a stimulation routine to the neurostimulator; receive one or more inputs that are indicative of a patient's response to execution of the stimulation routine by the neurostimulator; and display on the computing device one or more symbols that are indicative of an effectiveness of the stimulation routine, wherein the one or more symbols are based on the received one or more inputs and are displayed at a position on the lead representation that corresponds to parameters of the stimulation routine.

The one or more inputs may include one or more of a type of a symptom of the patient, an anatomical position of the patient's symptom, and a rating of a severity of the patient's symptom. The one or more inputs may additionally or alternatively include one or more of a type of side effect caused by the stimulation routine, an anatomical position of the side effect, and a rating of a severity of the side effect. The graphical user interface may include a field that is configured to receive a baseline rating of a severity of a symptom of the patient when no stimulation is applied. The one or more symbols may include an improvement indicator that is based on a difference between the baseline rating and a rating of a severity of the symptom when the stimulation routine is executed by the neurostimulator, and a color of the improvement indicator may be determined based on the difference between the baseline rating and the rating of the severity of the symptom when the stimulation routine is executed by the neurostimulator. The one or more symbols may additionally or alternatively include a side effect indicator that is based on a severity of one or more side effects caused by the execution of the stimulation routine by the neurostimulator, and a color of the side effect indicator may be determined based on the severity of the one or more side effects caused by the execution of the stimulation routine by the neurostimulator. The improvement indicator may be a circle and the side effect indicator may be a ring around the circle.

Each lead representation may include one or more electrode representations, and at least one of the electrode representations may be a segmented electrode representation that represents a set of the segmented electrodes. Each of the electrode representations may include an origin and one or more spokes that extend outward from the origin, and each spoke of a segmented electrode representation may extend from the origin in a direction that corresponds to a position of one of the segmented electrodes about the electrode lead. The graphical user interface may include at least one orientation adjuster to adjust an orientation of the one or more lead representations to match an orientation in which the one or more electrode leads are implanted in the patient, and the one or more orientation adjusters may rotate the spokes of a lead representation's electrode representations about their origin. Each of the spokes may be a stimulation amplitude axis, and the one or more symbols may be displayed along the one or more axes. The one or more inputs may be user inputs or they may be received from one or more sensors. The neurostimulator may be an implantable medical device that is configured to be implanted in the patient or it may be an external trial stimulator.

BRIEF DESCRIPTION OF THE DRAWINGS

FIG. 3 shows implantation of the IPG in a patient in a Deep Brain Stimulation (DBS) application in accordance with the prior art.

FIG. 4 shows an electrode lead having segmented electrodes as may be used in a DBS application in accordance with the prior art.

FIG. 5 shows components of a clinician's programmer system, including components for communicating with neurostimulator in accordance with the prior art.

FIGS. 7A-7C illustrate different types of lead representations that may be presented via the graphical user interface in accordance with an aspect of the disclosure.

FIG. 11 illustrates the graphical user interface of FIG. 6 with recorded effects of stimulation presented on one of the lead representations in accordance with an aspect of the disclosure.

FIG. 13 illustrates an example spreadsheet that includes recorded patient responses to stimulation routines in accordance with an aspect of the disclosure.

DETAILED DESCRIPTION

Figure 1:
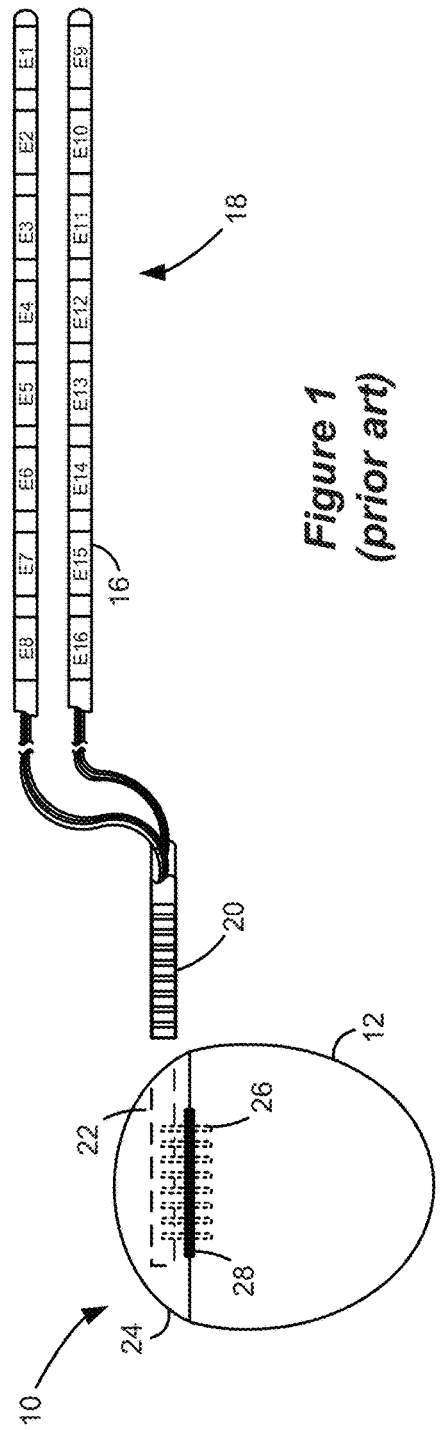
FIG. 1 shows an implantable pulse generator (IPG) with an electrode array in accordance with the prior art.
Figure 2:
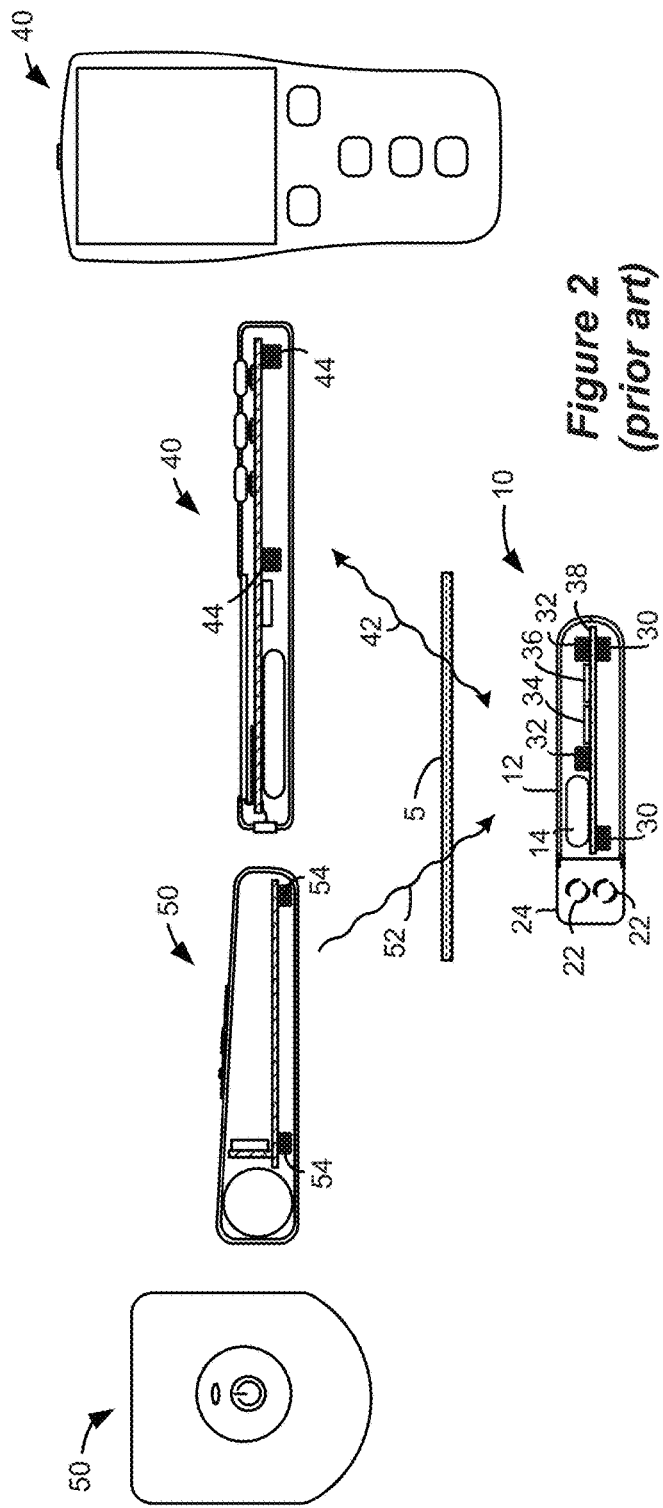
FIG. 2 shows a cross section of the IPG of FIG. 1 as implanted in a patient, as well as external devices that support the IPG, including an external charger and external controller in accordance with the prior art.
Figure 6:
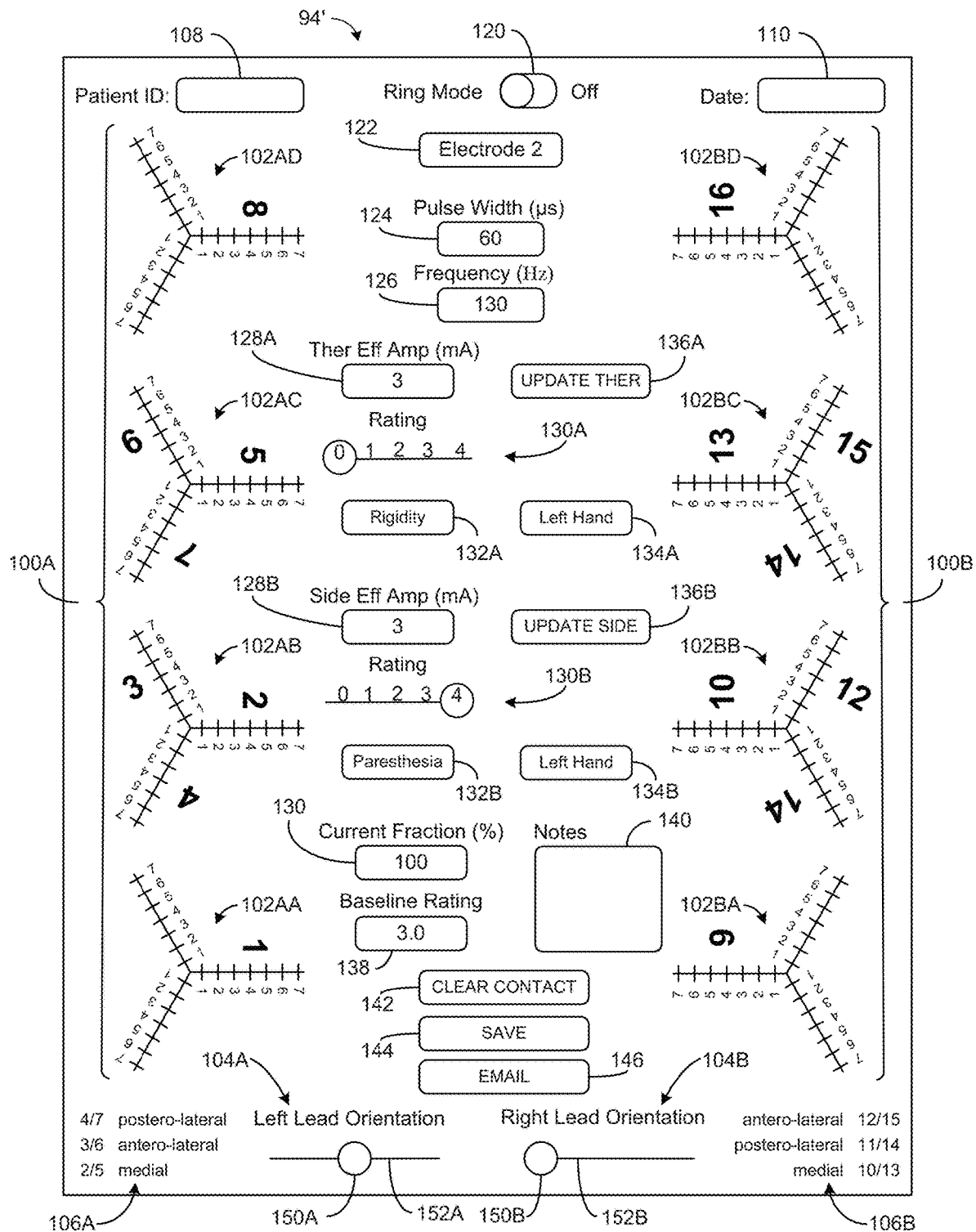
FIG. 6 shows an example graphical user interface that enables a visualization of the efficacy of DBS stimulation using one or more leads having segmented electrodes in accordance with an aspect of the disclosure.

FIG. 6 illustrates an improved CP GUI 94' that is rendered through the execution of improved CP software 96'. The interface 94' allows for the visualization of the efficacy of DBS stimulation applied using an electrode lead having segmented electrodes that enable directional control of applied stimulation. The interface 94' includes fields to enter patient information, fields to view and/or change the stimulation currently being provided to the patient, fields to receive inputs that are indicative of the patient's response to the stimulation, and graphical representations of the implanted leads on which symbols representing recorded therapeutic and side effects are presented to provide a visualization of the efficacy of different stimulation routines.

The graphical representations include a representation 100A of a first implanted lead and a representation 100B of a second implanted lead. In the example shown, the representation 100A corresponds to a lead implanted in the patient's left brain hemisphere and the representation 100B corresponds to a lead implanted in the patient's right brain hemisphere, but the labels of the leads may be customizable to allow for different implantation scenarios. Each lead representation 100 includes multiple electrode representations 102, which include one or more spokes that extend outward from an origin. The origin represents the axial location of the one or more electrodes corresponding to the electrode representation 102 along the lead. In the illustrated embodiment, the vertical position of an origin represents the inferior-superior position of its corresponding electrodes along the electrode lead. A set of electrodes represented by an origin nearer to the top of the interface 94' is superior to (i.e., less deeply implanted) than a set of electrodes represented by an origin nearer to the bottom of the interface 94'.

For segmented electrodes, each spoke corresponds to a single electrode and extends in a direction that represents the position of the segmented electrode about the lead. For circumferential electrodes, all of the spokes extending from an origin correspond to the same electrode. While a single one of the spokes extending from an origin corresponding to a circumferential electrode is labeled with the identifier of the circumferential electrode (e.g., circumferential electrode representations 102AA, 102AD, 102BA, and 102BD), each of the spokes extending from an origin corresponding to segmented electrodes is labeled with the electrode's identifier (e.g., segmented electrode representations 102AB, 102AC, 102BB, and 102BC). This enables electrode representations 102 to be identified as corresponding to either a circumferential electrode or a set of segmented electrodes.

The lead representations 100A/B illustrate electrodes located at four different axial positions along the lead with the middle two axial positions having three segmented electrodes each and the outer two axial positions having a single circumferential electrode each. These lead representations 100A/B correspond to the lead 18' (FIG. 4). The lead representations 102 that are presented via the interface 94' are based on a lead type selected via the CP software 96', and leads having different electrode arrangements can also be depicted via the interface 94' using different representations.

FIGS. 7A-7C illustrate lead representations for example leads having different electrode arrangements. The lead representation 202 in FIG. 7A corresponds to a lead having eleven electrodes. The electrodes are arranged at three different axial positions along the lead. The outer axial positions each include three segmented electrodes, and the middle axial position includes five segmented electrodes. The lead representation 204 in FIG. 7B corresponds to a lead having 12 electrodes. The electrodes are arranged at four axial positions along the lead that each include three segmented electrodes. The lead representation 206 in FIG. 7C corresponds to a lead having 14 electrodes. The electrodes are arranged at three different axial positions along the lead. The outer axial positions each include a single circumferential electrode, and the middle axial position includes 12 segmented electrodes. It will be understood that lead representations can be created for practically any electrode arrangement.

The orientation of the lead representations can be adjusted via the interface 94' so that the spokes corresponding to segmented electrodes extend in a direction corresponding to their anatomical position as implanted. In the illustrated embodiment, a spoke that extends vertically upward from an origin represents an electrode that is aligned with the sagittal plane in which the lead is implanted in a direction that is anterior to the coronal plane in which the lead is implanted, a spoke that extends vertically downward from an origin represents an electrode that is aligned with the sagittal plane in which the lead is implanted in a direction that is posterior to the coronal plane in which the lead is implanted, and a spoke that extends horizontally (either left of right) from an origin represents an electrode that is aligned with the coronal plane in which the lead is implanted. The orientation of lead representations 100A/B can be adjusted using the orientation adjusters 104A/B. In the illustrated embodiment, each orientation adjuster 104 includes a slider 150 positioned along a horizontal track 152. Movement of the slider 150 along the horizontal path 152 rotates each of the electrode representations associated with the corresponding lead representation about its origin.

Figures 8A, 8B, 8C:
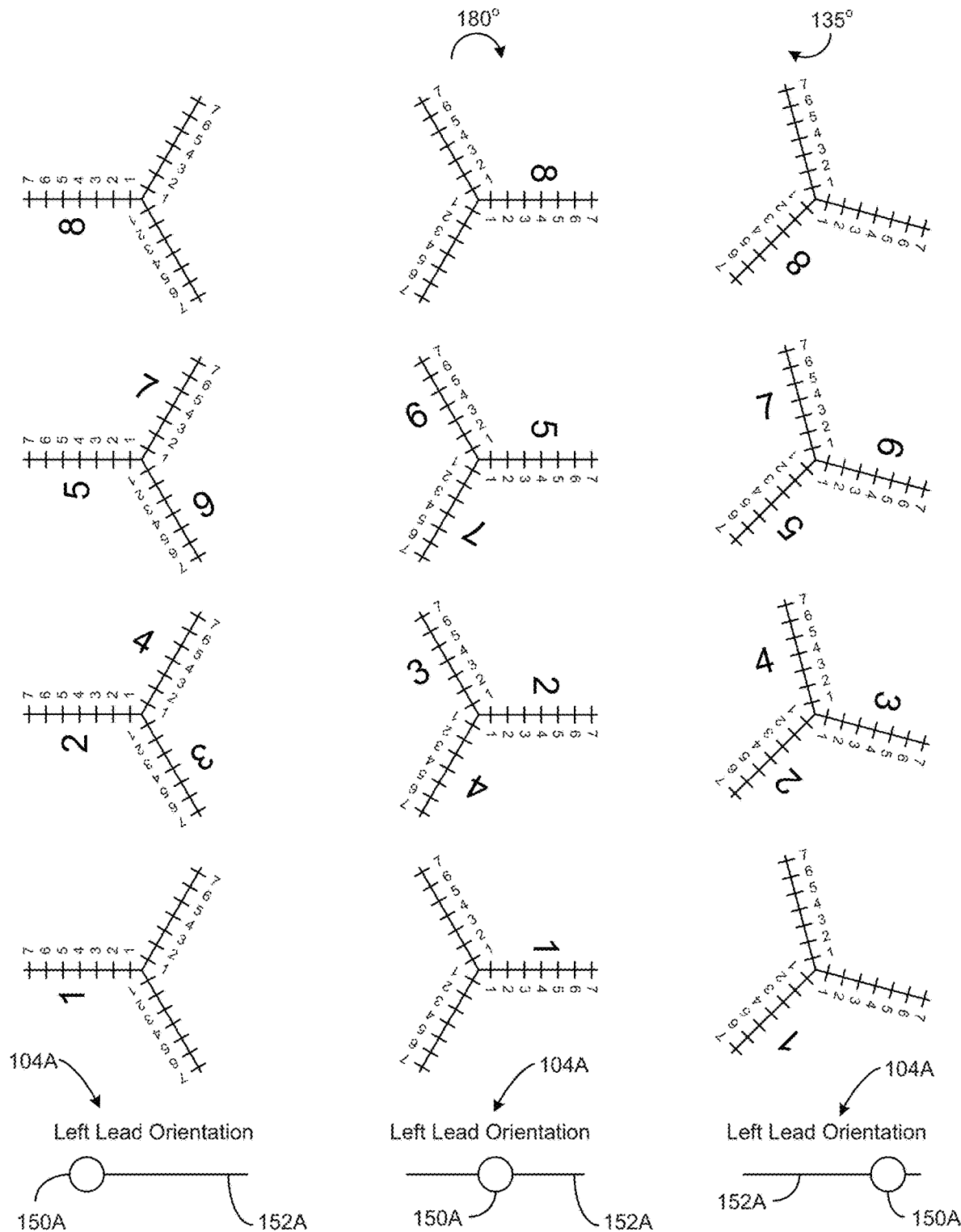
FIGS. 8A-8C illustrate the use of a lead orientation adjuster to adjust a lead representation that is presented via a graphical user interface in accordance with an aspect of the disclosure.

FIGS. 8A-8C show an example use of the orientation adjuster 104. In FIG. 8A, the slider 150 is positioned at the far left of the track 152, and the spokes corresponding to segmented electrodes 2 and 5 extend directly left from their respective origins. In FIG. 8B, the slider 150 is positioned at the exact midpoint of the track 152, and the spokes corresponding to segmented electrodes 2 and 5 extend directly right from their respective origins (a 180 degree rotation from the orientation shown in FIG. 8A). In FIG. 8C, the slider 150 is positioned 87.5% of the track 152's length away from the far left of the track 152. In this position, the spokes corresponding to electrodes 2 and 5 have rotated clockwise 315 degrees from the orientation shown in FIG. 8A. When the slider 150 is positioned at the far right of the track 152, the orientation of the lead representation 100 matches the orientation when the slider 150 is positioned at the far left of the track 152. While the illustrated orientation adjusters 104 include sliders 150, the interface 94' may additionally or alternatively include other orientation adjusters such as a numerical entry field for supplying an angular offset.

As noted above, DBS leads typically include a marker (such as marker 46) that enables identification of the orientation of the lead as implanted in the patient. After the implantation of one or more DBS leads, anteriorposterior and lateral radiological images of the implanted leads are typically acquired. The location of the lead marker 46 in these radiological images identifies the orientation of the lead. Using this information, the improved CP software 96' enables a user to select the type of lead that has been implanted (e.g., from a list of leads) and to adjust the orientation of the lead such that the interface 94' provides a visualization of the anatomical position of the leads' electrodes as implanted in the patient.

Referring back to FIG. 6, the interface 94' additionally includes a textual description of the orientation of the various segmented electrodes that updates based on the orientation selected using the orientation adjusters 104. Each textual description may correspond to a range of azimuthal positions, and the one or more electrodes falling into a particular azimuthal range may be labeled with the corresponding description. In the illustrated embodiment, segmented electrodes are labeled as postero-lateral, antero-lateral, or medial based on the selected orientation. Alternative or additional textual descriptions may also be provided.

Turning now to the use of the interface 94' to record information regarding a patient's response to different DBS stimulation routines, the interface 94' includes a patient ID field 108 and a date field 110 that enable a user to enter an identifier, such as a patient name or number, and a date of the fitting procedure. The data entered in these fields allows the fitting results to be linked to and stored along with the patient's medical records. The interface 94' additionally includes a number of stimulation fields that identify the parameters of a stimulation routine that has been communicated to and that is being executed by the IPG 10. These stimulation fields include the electrode field 122, the pulse width field 124, the frequency field 126, the current fraction field 130, the therapeutic effect amplitude field 128A, the side effect amplitude field 128B, and the ring mode indicator 120. The electrode field 122 includes a list of the available electrodes, which electrodes correspond to the identifiers in the lead representations 100A/B. For example, in the illustrated embodiment, the selection of electrode 2 in the electrode field 122 corresponds to the medial electrode in electrode representation 102AB bearing the same identifier.

When an electrode is selected via the electrode field 122, the other stimulation fields populate with the parameters of the currently-executing stimulation routine as it pertains to the selected electrode. In the illustrated embodiment, the stimulation fields indicate that electrode 2 is receiving 100% (current fraction field 130) of the total stimulation current of 3 mA (therapeutic effect amplitude field 128A and side effect amplitude field 128B, which mirror one another) and that stimulation pulses on electrode 2 have a pulse width of 60 microseconds (pulse width field 124) and a frequency of 130 Hz (frequency field 126). In ring mode, a group of segmented electrodes at the same axial position are utilized in conjunction to simulate the effect of a single circumferential electrode. Ring mode field 120 indicates that electrode 2 is not being used in this manner.

In one embodiment, the stimulation fields may enable data entry. That is, the stimulation fields may be editable such that a value entered into one of the stimulation fields is communicated to the IPG 10 and alters the stimulation routine that is being executed by the IPG 10. In another embodiment, the stimulation routine that is being executed by the IPG 10 may be altered from a different interface provided by the CP software 96', and the stimulation fields on the interface 94' may only display the current stimulation parameters.

The therapeutic effect symptom field 132A enables the user to select a particular type of symptom for which a rating is being entered. The field 132A may include a list of symptoms such as rigidity, bradykinesia, tremor, gait, turning, posture, freezing, arm swing, balance, and dystonia. The therapeutic effect symptom anatomical position field 134A enables the user to select an anatomical position of the selected symptom from a list including, for example, left hand, right hand, left arm, right arm, left leg, right leg, left foot, right foot, face, head, and torso, although an anatomical position need not be selected and may not be applicable for certain symptoms.

The therapeutic effect rating scale 130A enables the user to record a rating of the severity of the selected symptom. In the illustrated embodiment, the scale 130A enables the entry of values using the Uniform Parkinson's Disease Rating Scale (UPDRS). The UPDRS is a standard that associates a numerical value between zero and four with different severity levels of various symptoms of neurological disorders. While the illustrated scale 130A utilizes the UPDRS scale, other rating scales could also be utilized. In the illustrated embodiment, the therapeutic effect rating scale 130A includes a slider that enables the selection of the UPDRS value that represents the severity of the selected symptom of the patient's neurological disorder for the current stimulation routine. The user can thus position the slider at the appropriate location to select the value that represents the severity of the patient's symptom. Although the UPDRS scale recognizes only integer values between zero and four, the therapeutic effect rating scale 130A may enable the selection of values with a higher level of granularity (e.g., increments of 0.5).

The baseline rating field 138 enables the entry of a severity rating for a symptom selected via the symptom field 132A when no stimulation is being applied. The baseline rating can be entered for multiple different symptoms, and a previously entered baseline rating is displayed in the baseline rating field 138 when the corresponding symptom is selected via the symptom field 132A.

Side effects caused by a given stimulation routine can be entered and recorded in a similar manner to therapeutic effects. Like the therapeutic effect rating scale 130A, the side effect rating scale 130B includes a slider that enables the selection of a UPDRS value; however, the value selected via the side effect rating scale 130B represents the severity of a side effect caused by execution of a stimulation routine as opposed to the severity of a particular symptom of the patient's neurological disorder. The specific type of side effect for which a side effect rating is being entered can be selected via the side effect symptom field 132B. The side effect symptom field 132B may enable the selection of a side effect from a list including, for example, speech, paresthesia, muscle pulling, discomfort, ocular effect, dyskinesia, mania, dizziness, dystonia, depression, and nausea. The side effect symptom anatomical position field 134B enables the selection of an anatomical position of the selected side effect from a list that includes the same anatomical positions that can be selected via the therapeutic effect anatomic position field 134A. As with therapeutic effects, an anatomical position need not be selected and may not be applicable for certain side effects. There is no baseline rating corresponding to side effects as the side effects are, by definition, caused by stimulation and are therefore absent when stimulation is not being applied.

While the therapeutic effect, side effect, and baseline ratings have been described as user inputs, the ratings may also be generated, in whole or in part, based on inputs from one or more sensors that are applied to or otherwise observe the patient. For example, the CP computer 202 may receive inputs from one or more sensors such as accelerometers, cameras, or force sensors that can be translated into ratings of the severity of the patient's symptoms or side effects. Thus, the therapeutic effect, side effect, and baseline ratings may be automatically generated (either fully or partially) based on inputs from sensors.

The notes field 140 enables the user to associate a textual description with a recorded therapeutic or side effect. Selection of the notes field 140 may enable entry of text via a keyboard connected to the CP computer 202 or via an on-screen keyboard that is displayed upon selection of the notes field 140.

Therapeutic effects and side effects can be recorded and associated with the currently-executing stimulation routine using the selectors 136A and 136B. The "UPDATE THER" selector 136A associates the values in the therapeutic effect symptom field 132A, the anatomical position field 134A, the therapeutic effect rating 130A, and the notes field 140 with the current stimulation routine parameters as indicated via the stimulation fields. Similarly, the "UPDATE SIDE" selector 136B associates the values in the side effect symptom field 132B, the anatomical position field 134B, the side effect rating 130B, and the notes field 140 with the current stimulation routine parameters. Upon selection of either selector 136A or 136B, the associated values (i.e., stimulation values, notes, and either therapeutic or side effects entries depending on which selector is used) are stored in a memory in the CP computer 202. Because the data entered in the notes field is recorded each time either selector 136A/B is used, in one embodiment, the notes field 140 may be cleared when either selector 136A/B is utilized so that notes are not unintentionally recorded with a subsequent entry. Effects that are recorded using either selector 136A or 136B may be deleted using the clear contact selector 142, which may be configured to erase the last recorded effect or all recorded effects associated with the current electrode selection.

In a typical DBS fitting procedure, stimulation is provided between one or more lead-based electrodes 16 and the IPG 10's case 12. A user may typically select a standard pulse width and frequency (e.g., 60 microseconds and 130 Hz) and progress through the available electrodes 16 at different stimulation amplitudes in order to evaluate the effect of electrode selection and stimulation amplitude on the patient's response. For example, the user may initially stimulate using electrode 1 at each of multiple stimulation amplitudes (e.g., 0.5-6 mA in 0.5 mA steps), observing and recording the patient's response to each different stimulation routine, and then repeat the same process using electrode 2, and so on for each of the available electrodes 16. In one embodiment, the CP software 96' may include an automatic fitting routine that proceeds through different stimulation routines in such an order. In such an embodiment, the interface 94' may include a "pause" button that enables the user to pause the advancement through the various routines to record the effects of the currently-executing routine.

Figure 9A:
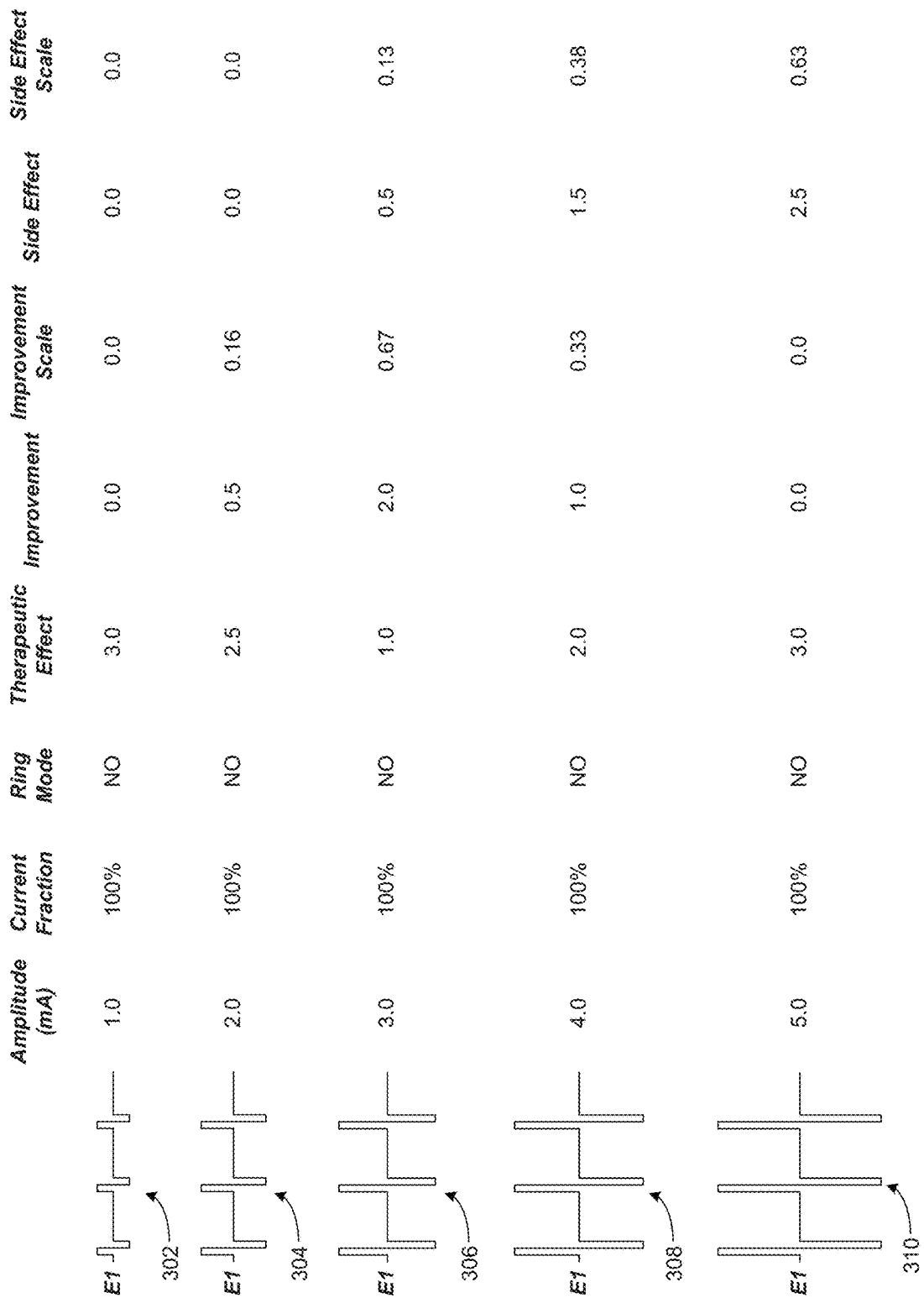
FIGS. 9A-9C illustrate example stimulation routines and recorded patient responses to the stimulation routines in accordance with an aspect of the disclosure.
Figure 9B:
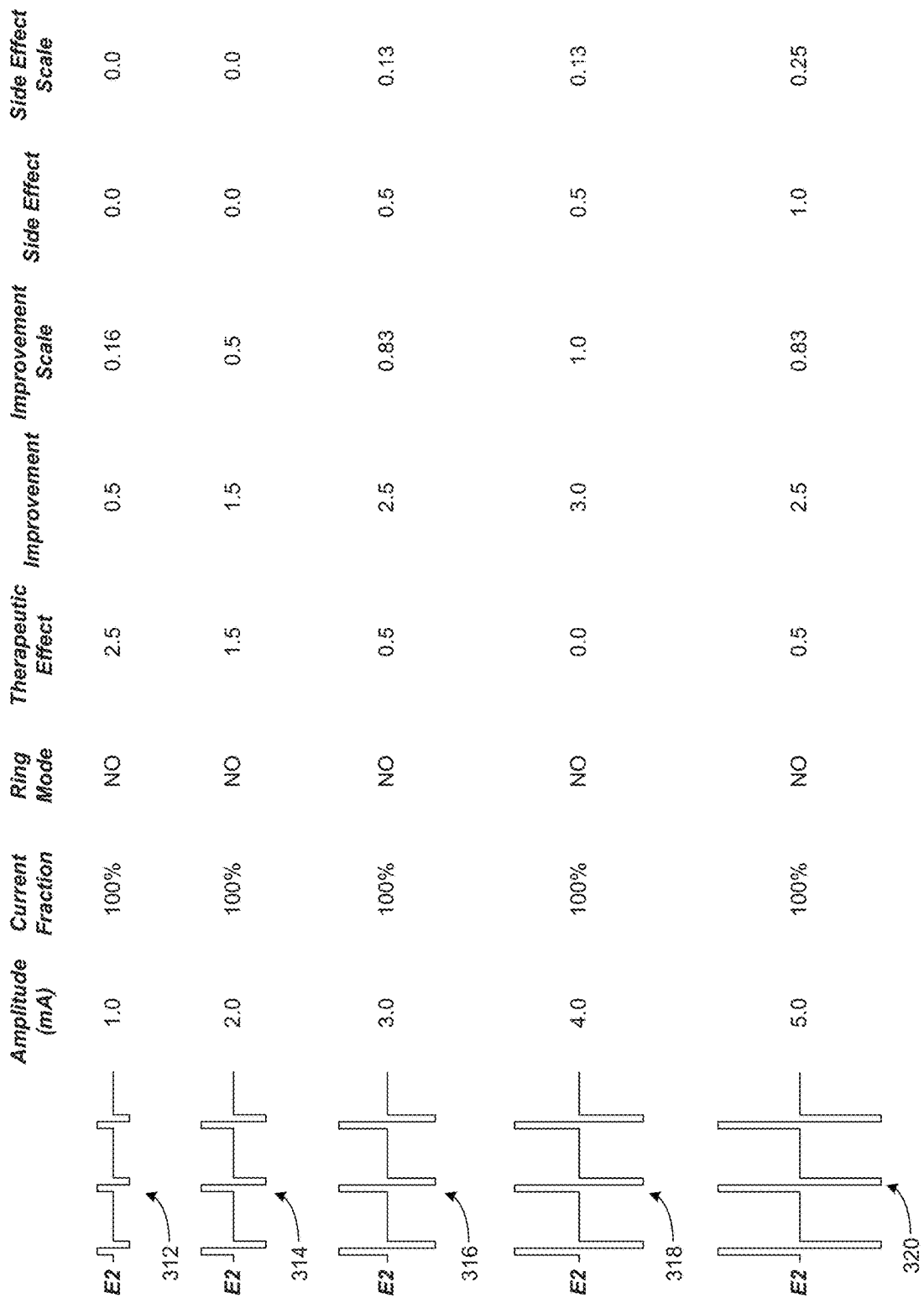
Figure 9C:
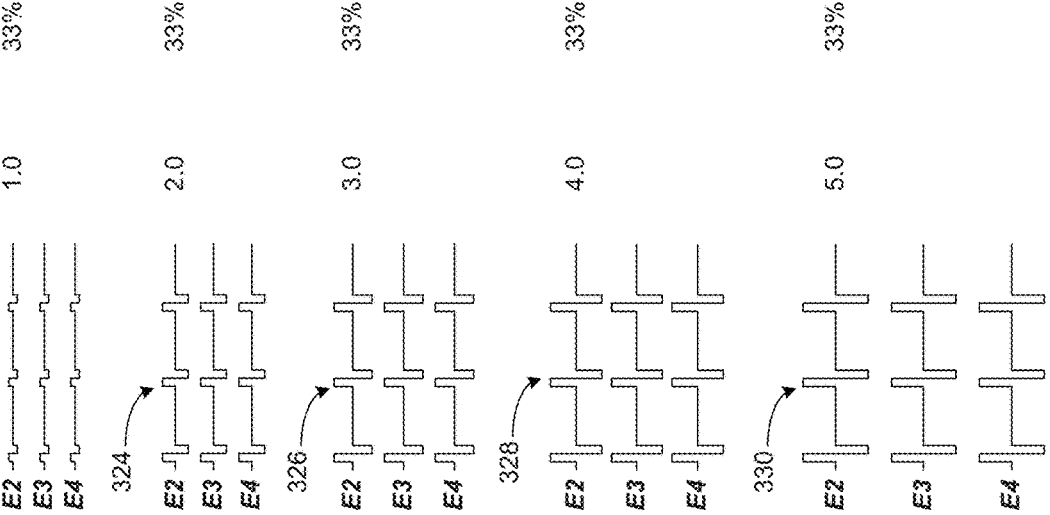

FIGS. 9A-9C illustrate a portion of an example DBS fitting sequence for a patient that exhibits a tremor with a severity rating of 3.0 when no stimulation is applied (i.e., the patient has a baseline tremor rating of 3.0). The example DBS fitting sequence is conducted with a fixed pulse width and frequency and with stimulation occurring between various electrodes 16 and the IPG's case 12. The examples shown in FIGS. 9A-9C illustrate stimulation routines that include a sequence of biphasic pulses applied using different electrodes and at different stimulation amplitudes. In each stimulation pulse, one or more selected electrodes 16 act as a stimulation anode during a stimulation phase of the pulse and as a stimulation cathode during an active recovery phase of the pulse. Stimulation patterns are only illustrated for the lead-based electrodes 16, but it will be understood that the IPG's case 12 is stimulated at an equal magnitude and opposite polarity to the one or more electrodes 16.

FIG. 9A illustrates recorded therapeutic effects, side effects, and related calculated values for monopolar stimulation delivered via electrode 1 at various stimulation amplitudes. The calculated values include an improvement value, an improvement scale value, and a side effect scale value. The improvement value is a measure of the improvement in a patient's symptoms as a result of stimulation, and it is equal to the patient's baseline rating minus the recorded therapeutic effect rating. The improvement scale value is a ratio of the improvement value to the patient's baseline rating. The side effect scale value is a ratio of the side effect rating to a maximum side effect rating. As described in greater detail below, the improvement scale value and the side effect scale value are utilized to provide a visualization of the efficacy of various stimulation routines via the interface 94'.

As shown in the table in FIG. 9A, when electrode 1 is utilized to provide stimulation at an amplitude of 1.0 mA (stimulation routine 302), a therapeutic effect rating of 3.0 and a side effect rating of 0.0 are recorded. The therapeutic effect rating of 3.0 indicates that the stimulation routine 302 provides no improvement in the severity of the patient's tremor as compared to the baseline rating. This translates to an improvement value of 0.0. Because there is no therapeutic improvement or side effects, the improvement scale value and the side effect scale value are both equal to 0.0.

When the stimulation amplitude is increased to 2.0 mA (stimulation routine 304), a therapeutic effect rating of 2.5 and a side effect rating of 0.0 are recorded. The therapeutic effect rating of 2.5 indicates a slight improvement in the severity of the patient's tremor, which translates to an improvement value of 0.5. The improvement scale value is equal to 0.16 (the ratio of the 0.5 improvement value to the 3.0 baseline value). Although the example values are based on a single symptom (i.e., tremor), values may also be computed based on the change in multiple symptoms as a result of stimulation. For example, the improvement value may be equal to the difference between the sum of the baseline ratings for multiple symptoms and the sum of the recorded therapeutic effect ratings for those symptoms. Similarly, the improvement scale value may utilize the sum of the baseline ratings for the multiple symptoms as its denominator. Because there are no recorded side effects, the side effect scale value for the stimulation routine 304 is equal to 0.0.

When the stimulation amplitude is increased to 3.0 mA (stimulation routine 306), a therapeutic effect rating of 1.0 and a side effect rating of 0.5 are recorded. The therapeutic effect rating of 1.0 translates to an improvement value of 2.0 and an improvement scale value of 0.67. The side effect scale value is equal to the ratio of the side effect value to the maximum side effect value. The maximum side effect value can be selected in different manners. In the illustrated example, the side effect value is based on a single recorded side effect and therefore the maximum side effect value is chosen to be equal to the maximum value of the single recorded side effect (i.e., 4.0), which results in a side effect scale value of 0.13. While the illustrated example is based on a single recorded side effect, multiple side effects can be recorded and their values summed to obtain the side effect value. When multiple side effects are recorded, the maximum side effect value may be determined to be equal to the sum of the maximum values for each of the side effects that are recorded (e.g., 8.0 for two recorded side effects, 12.0 for three recorded side effects, etc.). In another embodiment, the maximum side effect value may dynamically adjust to the highest recorded side effect value for the patient such that all side effect values are compared against the stimulation routine that resulted in the most severe side effects. This technique would result in the most severe recorded side effect always having a side effect scale value of 1.0.

When the stimulation amplitude is increased to 4.0 mA (stimulation routine 308), a therapeutic effect rating of 2.0 and a side effect rating of 1.5 are recorded. The therapeutic effect rating results in an improvement value of 1.0 and an improvement scale value of 0.33, and the side effect rating results in a side effect scale value of 0.38. Note that stimulation at 4.0 mA results in a decrease in the beneficial effect as compared to stimulation at 3.0 mA as well as an increase in side effects.

When the stimulation amplitude is increased to 5.0 mA (stimulation routine 310), a therapeutic effect rating of 3.0 and a side effect rating of 2.5 are recorded. The therapeutic effect rating results in an improvement value of 0.0 and an improvement scale value of 0.0, and the side effect rating results in a side effect scale value of 0.63. Thus, there is no therapeutic benefit of stimulation at 5.0 mA as compared to the patient's baseline rating, and such stimulation comes with significant side effects.

In FIG. 9B, the therapeutic and side effect ratings and calculations are illustrated for monopolar stimulation utilizing segmented electrode 2. As shown in FIG. 9B, this type of stimulation results in a therapeutic effect rating of 0.0 at a stimulation amplitude of 4.0 mA. Side effects are observed beginning at a stimulation amplitude of 3.0 mA and they increase in severity with increasing stimulation amplitude.

FIG. 9C illustrates the same types of information as FIGS. 9A and 9B for ring mode stimulation using electrodes 2-4, in which stimulation current is divided equally between the electrodes. Each of electrodes 2-4 receives one-third of the specified current amplitude. As illustrated, the improvement value increases with increasing stimulation amplitude. Side effects are observed beginning at a stimulation amplitude of 3.0 mA and they increase in severity with increasing stimulation amplitude.

Figure 10A:
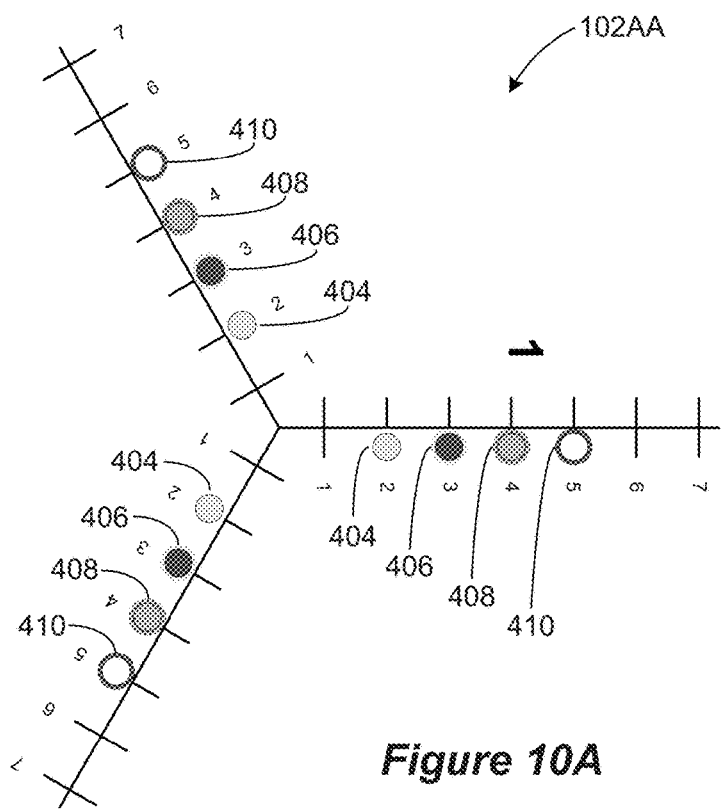
FIGS. 10A-10B illustrate the display of symbols that depict recorded effects of stimulation on electrode representations that are presented via a graphical user interface in accordance with an aspect of the disclosure.
Figure 10B:
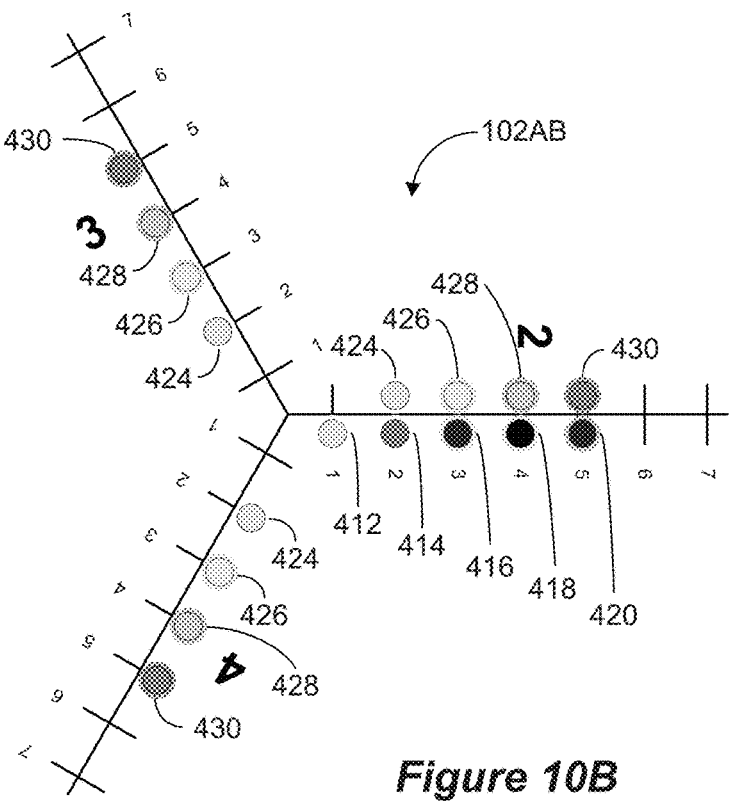

The therapeutic and side effects that are recorded via the interface 94' are utilized to display one or more symbols that are indicative of an effectiveness of the stimulation routines at a position on the lead representation that corresponds to parameters of the stimulation routine. FIGS. 10A and 10B illustrate an example of the type of visualization that is provided via the interface 94' for the example stimulation routines and effects illustrated in FIGS. 9A-9C. FIG. 10A illustrates the electrode representation 102AA that corresponds to electrode 1, and FIG. 10B illustrates the electrode representation 102AB that corresponds to electrodes 2-4. Each spoke of an electrode representation is a stimulation amplitude axis that increases from the origin outward. In the illustrated embodiment, the spokes are labeled in milliamp units. Effect markers that depict recorded effects of stimulation are plotted at locations that correspond to the electrode selection and the amplitude of the stimulation. Each effect marker includes an inner portion that represents a measure of therapeutic improvement (i.e., an improvement indicator) and an outer portion that represents a measure of side effects of stimulation (i.e., a side effect indicator). In the illustrated embodiment, a luminosity value of the inner region is set based on the improvement scale value and a luminosity value of the outer region is set based on the side effect scale value. The inner region varies from white to black with darker colors representing a larger therapeutic improvement (i.e., a higher improvement scale value) than lighter values. The outer region varies from white to black with darker values representing more significant side effects (i.e., a higher side effect scale value) than lighter values.

While the inner and outer regions of the effect markers in the illustrated embodiment reflect therapeutic improvement and side effects, respectively, using the same grayscale color scheme, in an alternate embodiment, the inner and outer regions may utilize different colors. For example, the inner region might represent a measure of therapeutic improvement via a saturation or luminosity level of a green color while the outer region might represent a measure of side effects via a saturation or luminosity level of a red color. In another embodiment, the measures of therapeutic improvement and side effects may be represented by the size of the inner and outer regions. It will be understood that the effect markers may include any symbol that provides a visual representation of different levels of therapeutic improvement and/or side effects. Moreover, while specific calculations have been described for the improvement scale value and the side effect scale value that determine the manner in which the effect markers are presented, it will be understood that measures of therapeutic improvement and side effects can be calculated in different ways and such different calculations can be utilized to determine the manner in which the effect markers are presented.

The effect markers corresponding to the recorded effects of the stimulation routines illustrated in FIG. 9A are plotted in the electrode representation 102AA in FIG. 10A. Because electrode 1 is a circumferential electrode, identical effect markers are positioned along the right side of each of the spokes extending from the electrode representation 102AA's origin. No therapeutic improvement or side effects were recorded for the stimulation routine 302 (stimulation amplitude=1.0 mA), so there is no effect marker at the location corresponding to 1.0 mA. The effect marker 404 at the 2.0 mA location along each spoke corresponds to the stimulation routine 304, and the colors of its inner and outer regions reflect the improvement scale value of 0.16 and the side effect scale value of 0.0, respectively. The effect marker 406 at the 3.0 mA location along each spoke corresponds to the stimulation routine 306, and the colors of its inner and outer regions reflect the improvement scale value of 0.67 and the side effect scale value of 0.13, respectively. The effect marker 408 at the 4.0 mA location along each spoke corresponds to the stimulation routine 308, and the colors of its inner and outer regions reflect the improvement scale value of 0.33 and the side effect scale value of 0.38, respectively. The effect marker 410 at the 5.0 mA location along each spoke corresponds to the stimulation routine 310, and the colors of its inner and outer regions reflect the improvement scale value of 0.0 and the side effect scale value of 0.63, respectively. A quick glance at the electrode representation 102AA shows that stimulation at 3.0 mA is more effective (i.e., a greater degree of improvement with lesser side effects) than the other stimulation amplitudes that are shown.

FIG. 10B illustrates the placement of the effect markers corresponding to the recorded effects of the stimulation routines illustrated in FIGS. 9B and 9C. As with FIG. 10A, the two least significant digits of the identifier for each effect marker matches the two least significant digits of the identifier of the stimulation routine with which it corresponds. For the monopolar stimulation utilizing electrode 2 shown in FIG. 9B, effect markers are only plotted along the spoke corresponding to electrode 2 (along the right side of the spoke). For the ring mode stimulation utilizing electrodes 2-4 shown in FIG. 9C, effect markers are plotted along the left side of the spokes corresponding to each of the electrodes 2-4. Note that effect markers corresponding to monopolar stimulation utilizing either electrode 3 or electrode 4 would be plotted along the right sides of the spokes for the corresponding electrode in the same manner as for the monopolar stimulation utilizing electrode 2.

Figure 11:
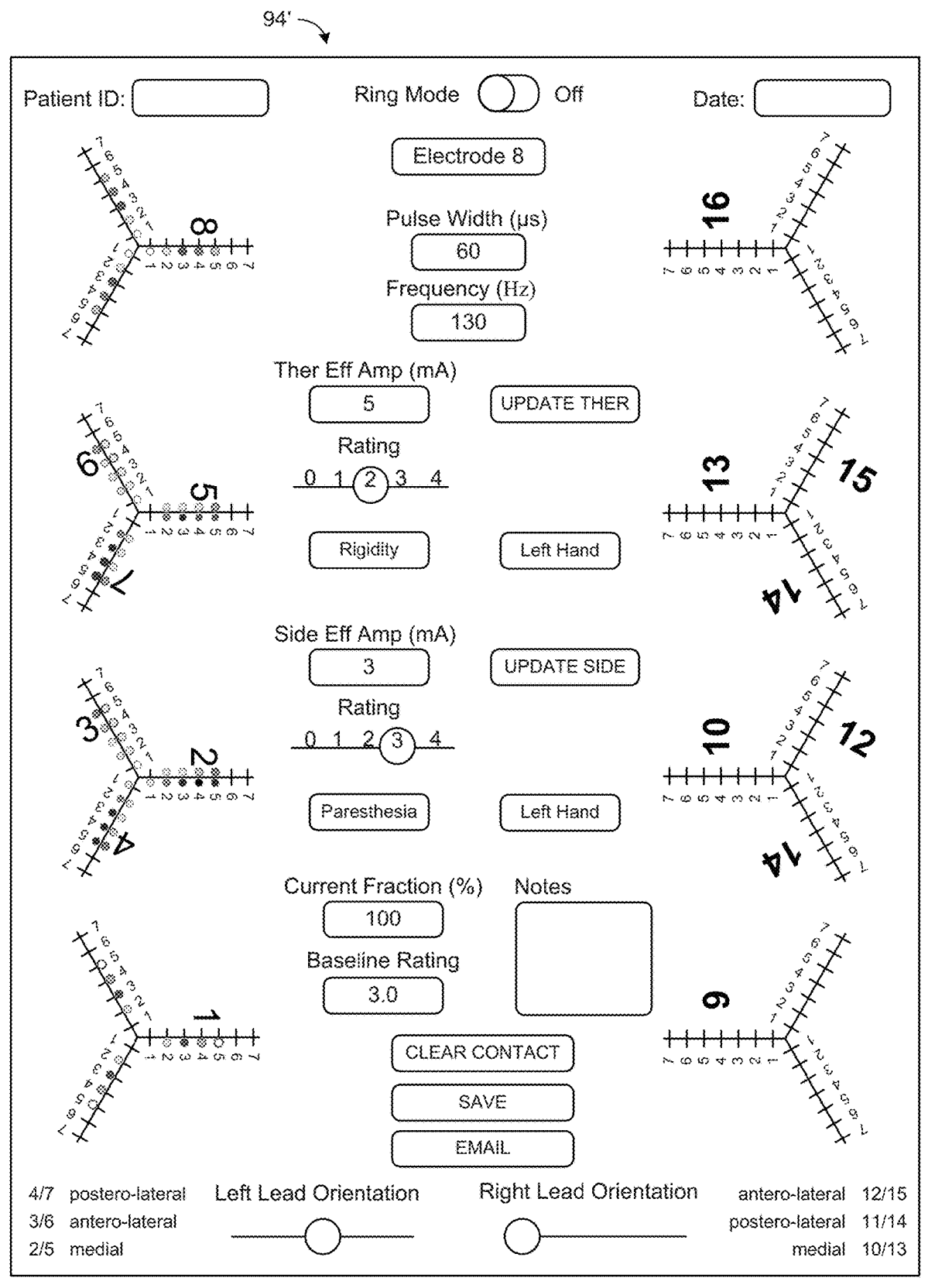
Figure 12:
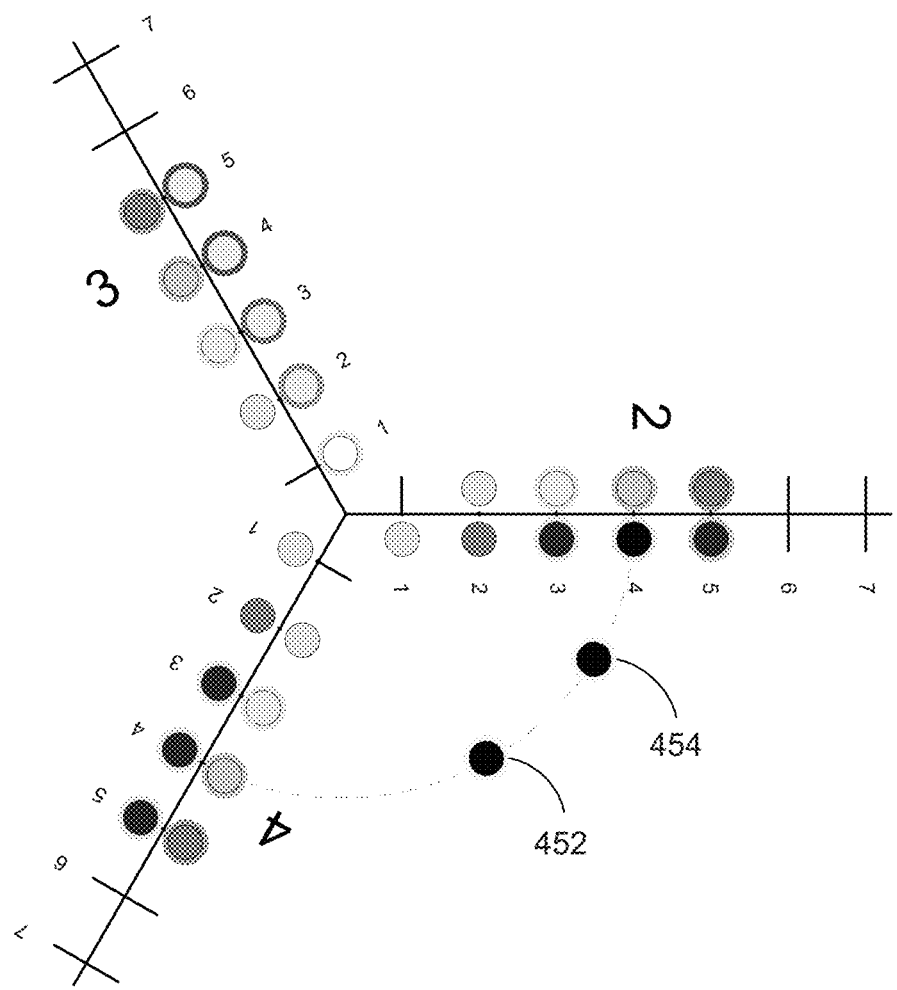
FIG. 12 illustrates an electrode representation that may be presented via the graphical user interface and the presentation of the effects of stimulation routines that are intended to fine-tune the stimulation that is provided to the patient in accordance with an aspect of the disclosure.

Visualizations such as those illustrated in FIGS. 10A and 10B provide a clear indication of the specific electrodes and stimulation amplitudes that provide efficacious therapy for the patient. After a quick, initial run-through of all of the available electrodes for a particular lead (e.g., the lead corresponding to lead representation 100A), a user may be presented with a view such as that illustrated in FIG. 11. Effect markers would also be populated on the lead representation 100B after a stimulation fitting procedure had been performed for its electrodes. Based on the visualization shown in FIG. 11, a user may observe that the most efficacious therapy is provided using the segmented electrodes 2, 4, 5, and 7. The user can then attempt to fine-tune therapy by using different ones of these electrodes in combination and/or more finely-tuned stimulation amplitudes (e.g., amplitudes in units of 0.1 mA). Therapeutic and side effects recorded for these additional fine-tuned stimulation routines can also generate an effect marker that is plotted on the lead representation. For example, the effect marker 452 in FIG. 12 results from stimulation using electrodes 2 and 4 at a stimulation amplitude of 4.0 mA with each electrode receiving 50% of the stimulation current. Similarly, the effect marker 454 results from stimulation using electrodes 2 and 4 at a stimulation amplitude of 4.0 mA with electrode 2 receiving 75% of the stimulation current and electrode 4 receiving the remaining 25% of the stimulation current. In this fine-tuning stage of the fitting procedure, the user might also adjust the pulse width and/or frequency that have previously been held constant.

Returning again to FIG. 6, the save selector 144 generates one or more files that include the results of the fitting procedure. The files can include pictures of the lead representations 100A/B with the plotted effect markers as well as one or more files (such as text, spreadsheet, and/or database files) that include each recorded therapeutic and side effect and any notes along with the associated stimulation parameters. The save selector may present a file path interface that enables the user to name the file and save it to a selected location (e.g., in the CP computer 202's local memory or to a networked storage location). The email selector 146 may function in a similar manner to the save selector 144 (i.e., it may generate the same one or more files), but it may additionally launch an email program with a new email message interface that is populated with the one or more files as attachments. The user can thus enter an email recipient and/or a message to transmit the results of the fitting procedure.

FIG. 13 illustrates an example spreadsheet 500 that might be generated through the selection of the save selector 144 or the email selector 146. In the illustrated embodiment, the first record in the dataset includes the patient ID and date entered via the interface 94'. The second record in the dataset includes column headings for the electrode, current fraction, pulse width, frequency, amplitude, therapeutic effect type, therapeutic effect anatomical position, therapeutic effect rating, side effect type, side effect anatomical position, side effect rating, and notes. The first five headings correspond to the parameters of a stimulation routine that is executed by the IPG 10 at the time a therapeutic effect or a side effect is recorded. The following three headings correspond to the data entered via the therapeutic effect fields 132A, 134A, and 130A, respectively, at the time the selector 136A is selected. The following three headings correspond to the data entered via the side effect fields 132B, 134B, and 130B, respectively, at the time the selector 136B is selected. The final heading corresponds to the data entered via the notes field 140 at the time either selector 136A or 136B is selected.

The first record under the headings includes the baseline rating, and each remaining record includes a recorded therapeutic effect or side effect along with its associated stimulation routine parameters. In the illustrated embodiment, a separate record is stored for each therapeutic effect or side effect that is entered via the interface 94'. Note that data records corresponding to ring mode stimulation (e.g., the stimulation routines shown in FIG. 9C) are stored with an entry in the electrode field that identifies each of the stimulation electrodes. It will be understood that data entered via the interface 94' could be stored in a number of different formats.

Figure 14:
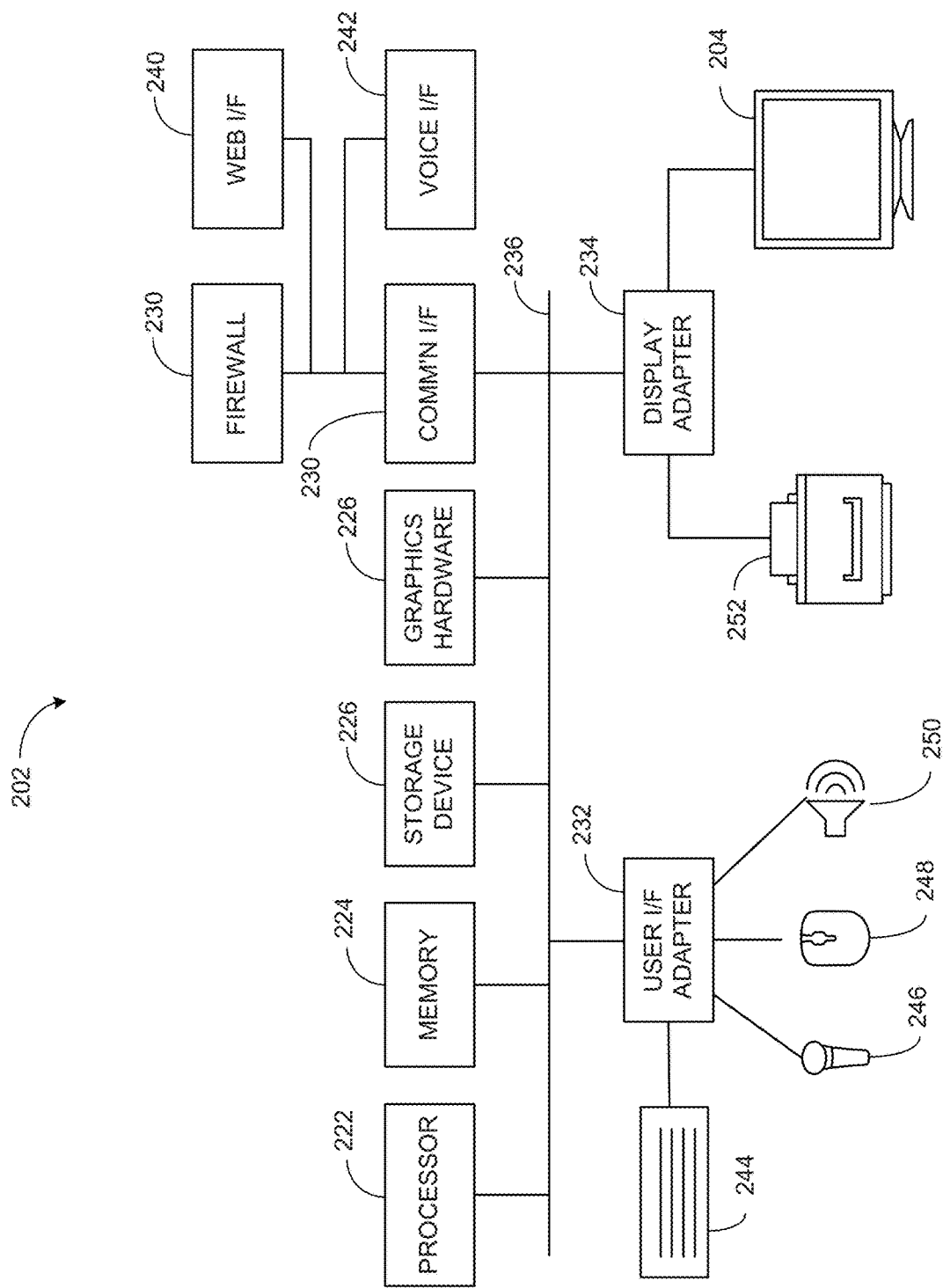
FIG. 14 illustrates a representative computing environment on which software that provides an interface for visualizing the efficacy of DBS stimulation may be executed in accordance with an aspect of the disclosure.

FIG. 14 illustrates the various components of an example CP computer 202 that may be configured to execute the improved CP software 96'. The CP computer 202 can include the processor 222, memory 224, storage 220, graphics hardware 228, communication interface 230, user interface adapter 232 and display adapter 234—all of which may be coupled via system bus or backplane 236. Memory 224 may include one or more different types of media (typically solid-state) used by the processor 222 and graphics hardware 228. For example, memory 224 may include memory cache, read-only memory (ROM), and/or random access memory (RAM). Storage 220 may store media, computer program instructions or software (e.g., CP software 96'), preference information, device profile information, and any other suitable data. Storage 220 may include one or more non-transitory computer-readable storage mediums including, for example, magnetic disks (fixed, floppy, and removable) and tape, optical media such as CD-ROMs and digital video disks (DVDs), and semiconductor memory devices such as Electrically Programmable Read-Only Memory (EPROM), Electrically Erasable Programmable Read-Only Memory (EEPROM), and USB or thumb drive. Memory 224 and storage 220 may be used to tangibly retain computer program instructions or code organized into one or more modules and written in any desired computer programming language. Communication interface 230 (which may comprise, for example, the ports 206 or 208) may be used to connect the CP computer 202 to a network. Communications directed to the CP computer 202 may be passed through a protective firewall 238. Such communications may be interpreted via web interface 240 or voice communications interface 242. Illustrative networks include, but are not limited to: a local network such as a USB network; a business' local area network; or a wide area network such as the Internet. User interface adapter 232 may be used to connect a keyboard 244, microphone 246, pointer device 248, speaker 250 and other user interface devices such as a touch-pad and/or a touch screen (not shown). Display adapter 234 may be used to connect display 204 and printer 252.

Processor 222 may include any programmable control device. Processor 222 may also be implemented as a custom designed circuit that may be embodied in hardware devices such as application specific integrated circuits (ASICs) and field programmable gate arrays (FPGAs). The CP computer 202 may have resident thereon any desired operating system.

While the CP system 200 has been described and illustrated as communicating directly with the IPG 10, the CP system 200 may additionally or alternatively be configured to communicate with different types of neurostimulators. For example, the CP system 200 may interface with an external trial stimulator that mimics the operation of the IPG 10 but that is positioned outside of the body to evaluate therapies during a trial phase. Moreover, while the improved software 96' has generally been described in the context of its use for an initial fitting procedure, it is equally applicable to the evaluation of different stimulation routines after the IPG 10 has been implanted for some time. As will be understood, the improved software 96' may be stored on a medium such as a CD or a USB drive, pre-loaded on a computing device such as the CP computer 202, or made available for download from a program repository via a network connection. As has been illustrated, the improved interface 94' provides a visualization of the efficacy of various DBS stimulation routines that employ electrode leads having one or more segmented electrodes.

Although particular embodiments have been shown and described, it should be understood that the above discussion is not intended to limit the present disclosure to these embodiments. It will be obvious to those skilled in the art that various changes and modifications may be made without departing from the spirit and scope of the present disclosure. Thus, the present disclosure is intended to cover alternatives, modifications, and equivalents that may fall within the spirit and scope of the claims.

What is claimed is:

1. A non-transitory computer-readable medium having instructions stored thereon to cause control circuitry in a computing device to:

generate a graphical user interface on a display of the computing device that includes a one or more representations of one or more electrode leads that are implantable in a patient's brain, wherein each lead representation comprises a representation of a position of each of a plurality of electrodes and an axis for each of the plurality of electrodes representing different values of a stimulation parameter applied to the respective electrode;

cause telemetry circuitry in the computing device to communicate a stimulation routine to a neurostimulator that is connected to the one or more electrode leads and specifies one of the electrodes and a value of the stimulation parameter;

receive one or more inputs that are indicative of a patient's response to execution of the stimulation routine by the neurostimulator; and display on the computing device, at the position of the specified one of the electrodes and at a position along the axis for the specified one of the electrodes corresponding to the specified value of the stimulation parameter, one or more non-textual, graphical symbols that are indicative of an effectiveness of the stimulation routine, wherein the one or more non-textual, graphical symbols are based on the received one or more inputs.

2. The medium of claim 1, wherein the one or more inputs comprise one or more of a type of a symptom of the patient, an anatomical position of the patient's symptom, or a rating of a severity of the patient's symptom.

3. The medium of claim 1, wherein the one or more inputs comprise one or more of a type of side effect caused by the stimulation routine, an anatomical position of the side effect, or a rating of a severity of the side effect.

4. The medium of claim 1, wherein the graphical user interface comprises a field that is configured to receive a baseline rating of a severity of a symptom of the patient when no stimulation is applied.

5. The medium of claim 4, wherein the one or more non-textual, graphical symbols comprise an improvement indicator that is based on a difference between the baseline rating and a rating of a severity of the symptom when the stimulation routine is executed by the neurostimulator.

6. The medium of claim 5, wherein a color of the improvement indicator is determined based on a difference between the baseline rating and the rating of the severity of the symptom when the stimulation routine is executed by the neurostimulator.

7. The medium of claim 5, wherein the one or more non-textual, graphical symbols comprise a side effect indicator that is based on a severity of one or more side effects caused by the execution of the stimulation routine by the neurostimulator.

8. The medium of claim 7, wherein a color of the side effect indicator is determined based on the severity of the one or more side effects caused by the execution of the stimulation routine by the neurostimulator.

9. The medium of claim 8, wherein the improvement indicator is a circle and the side effect indicator is a ring around the circle.

10. The medium of claim 1, wherein each lead representation comprises one or more electrode representations.

11. The medium of claim 10, wherein the electrodes comprise a plurality of segmented electrodes and at least one of the one or more electrode representations is a segmented electrode representation that represents a set of the segmented electrodes.

12. The medium of claim 11, wherein each of the one or more electrode representations comprises an origin and one or more spokes that extend outward from the origin.

13. The medium of claim 12, wherein each spoke of the segmented electrode representation extends from the origin in a direction that corresponds to a position of one of the segmented electrodes about the electrode lead.

14. The medium of claim 1, wherein each lead representation comprises one or more electrode representations that comprise an origin and one or more spokes that extend outward from the origin.

15. The medium of claim 14, wherein the graphical user interface comprises at least one orientation adjuster to adjust an orientation of the one or more lead representations to match an orientation in which the one or more electrode leads are implanted in the patient.

16. The medium of claim 15, wherein the one or more orientation adjusters rotate the spokes of a lead representation's electrode representations about their origin.

17. The medium of claim 14, wherein each of the spokes is a stimulation amplitude axis, and wherein the one or more non-textual, graphical symbols are displayed along the one or more spokes.

18. The medium of claim 1, wherein the one or more inputs are user inputs.

19. The medium of claim 1, wherein the one or more inputs are received from one or more sensors.

20. A system, comprising:
a neurostimulator; and
a non-transitory computer-readable medium having instructions stored thereon to cause control circuitry in a computing device to:
generate a graphical user interface on a display of the computing device that includes one or more lead representations of one or more electrode leads that are connected to the neurostimulator, wherein each lead representation comprises a representation of a position of each a plurality of electrodes and an axis for each of the plurality of electrodes representing different values of a stimulation parameter applied to the respective electrode;
cause telemetry circuitry in the computing device to communicate a stimulation routine to the neurostimulator and specifies one of the electrodes and a value of the stimulation parameter;
receive one or more inputs that are indicative of a patient's response to execution of the stimulation routine by the neurostimulator; and
display on the computing device, at the position of the specified one of the electrodes and at a position along the axis for the specified one of the electrodes corresponding to the selected value of the stimulation parameter, one or more non-textual, graphical symbols that are indicative of an effectiveness of the stimulation routine, wherein the one or more non-textual, graphical symbols are based on the received one or more inputs.

\* \* \* \* \*